(12) United States Patent
Huff

(10) Patent No.: US 12,263,376 B1
(45) Date of Patent: Apr. 1, 2025

(54) MICROSENSORS APPLIED TO ATHLETES BODIES IN ORDER TO PROVIDE REAL-TIME FEEDBACK ABOUT SPORT-SPECIFIC TECHNIQUE FOR SPORT PERFORMANCE IMPROVEMENTS

(71) Applicant: CORPORATION FOR NATIONAL RESEARCH INITIATIVES, Reston, VA (US)

(72) Inventor: Michael A. Huff, Oakton, VA (US)

(73) Assignee: Corporation for National Research Initiatives, Reston, VA (US)

( * ) Notice: Subject to any disclaimer, the term of this patent is extended or adjusted under 35 U.S.C. 154(b) by 338 days.

(21) Appl. No.: 17/528,970

(22) Filed: Nov. 17, 2021

(51) Int. Cl.
*A63B 24/00* (2006.01)

(52) U.S. Cl.
CPC .. *A63B 24/0006* (2013.01); *A63B 2024/0012* (2013.01); *A63B 2208/02* (2013.01); *A63B 2208/03* (2013.01); *A63B 2220/836* (2013.01); *A63B 2225/52* (2013.01)

(58) Field of Classification Search
CPC ........ A63B 24/0006; A63B 2024/0012; A63B 2208/02; A63B 2208/03; A63B 2220/836; A63B 2225/52
See application file for complete search history.

(56) References Cited

U.S. PATENT DOCUMENTS

| | | | |
|---|---|---|---|
| 6,870,466 B2* | 3/2005 | Rust | A63B 24/0021 340/565 |
| 9,855,484 B1* | 1/2018 | Matak | A61B 5/0022 |
| 10,201,292 B2* | 2/2019 | Sharpe | G09B 19/0038 |
| 10,223,557 B2* | 3/2019 | Malcolm | A63B 21/4039 |
| 10,486,049 B2* | 11/2019 | Nieminen | G06V 40/23 |
| 10,610,761 B1* | 4/2020 | Matak | H04Q 9/00 |
| 2003/0189484 A1* | 10/2003 | Rust | G09B 19/0038 340/539.23 |
| 2006/0098772 A1* | 5/2006 | Reho | A63B 71/0686 482/8 |
| 2014/0277628 A1* | 9/2014 | Nieminen | A63B 71/06 700/91 |
| 2015/0305655 A1* | 10/2015 | Sharpe | G09B 19/0038 702/141 |
| 2017/0361146 A1* | 12/2017 | Malcolm | A63B 69/0028 |
| 2019/0125219 A1* | 5/2019 | Sharpe | A63B 69/12 |
| 2022/0266091 A1* | 8/2022 | Yuen | G16H 20/30 |

* cited by examiner

*Primary Examiner* — Garrett K Atkinson
(74) *Attorney, Agent, or Firm* — Nixon & Vanderhye, P.C.

(57) ABSTRACT

A microsensor module includes: one or more microsensors; a power supply; communication circuit; and processing circuitry. The processing circuitry may be configured to: receive data measured by the one or more microsensors; process the measured data to determine a plurality of different performance parameters related to technique of an athlete when performing a sport; and output, using the communication circuit, real-time information about the correctness of technique and performance level of the athlete performing the sport, wherein the microsensor module is encapsulated in a water-proof package that is attachable or adjoinable to the athlete's body.

31 Claims, 21 Drawing Sheets

| | Size (mm x mm) | cost ($/ea) | Acceleration range (+/- g) | Output noise density (ug/sqrt(Hz)) | Sensitivity (mg/LSB) | BW (Hz) | Current (uA @2.4V) | Sleep Current (uA @2.4V) | Zero-g offset (+/- mg) |
|---|---|---|---|---|---|---|---|---|---|
| 1 | 2.2 | $4.00 | 2, 4, 8, 16 | 150 | 0.977 | 8-1000 | 6.5, 66, 130 | 1 | 80 |
| 2 | 3.3 | $2.63 | 2, 4, 8 | 100-130 | 0.244 | 2-800 | 8, 35, 240 | 2 | 30 |
| 3 | 2 | $3.16 | 2, 4, 8 | ~100 | 0.061 | 10-800 | 50, 120, 180 | 6 | 40 |

Table 1.

FIG. 20

| | Magnetic field range (+/- uT) | Heading Accuracy (+/- Deg) | Resolution (uT) | Output rate (Hz) | Current (uA @2.4V) | Sleep Current (uA @2.4V) | Zero-B offset (+/- uT) |
|---|---|---|---|---|---|---|---|
| 1 | 1300,2500 | 3 | 0.3 | 10-100 | 170,500,800 | 1 | 40 |
| 2 | 1200 | | 0.1 | 2-800 | 375,001,000 | 2 | 10 |
| 3 | >10000 | | 580 | 20 | 40,270 | 6 | 40 |

Table 2.

FIG. 21

MICROSENSORS APPLIED TO ATHLETES BODIES IN ORDER TO PROVIDE REAL-TIME FEEDBACK ABOUT SPORT-SPECIFIC TECHNIQUE FOR SPORT PERFORMANCE IMPROVEMENTS

FIELD OF INVENTION

The present invention is directed to microsensors and more particularly to the use of microsensors that are applied to various points on an athletes body during the performance of an athletic activity wherein the sensors measure and collect data about the athlete's technique during the performance of a sport, analyze this measured microsensor data, and provide the athlete and other interested parties with real-time information about their technique and skill level that allows the athlete to know how to improve their sports-specific technique, skill and performance.

BACKGROUND OF THE INVENTION

In many forms of athletic endeavors and competition, the technique and skill used in the sport are incredibly important to the athlete's performance level relative to other athletes. However, it can be extremely difficult even for elite athletes to always know exactly how to improve their technique so as to better their performance. Many sports, such as swimming, golf, gymnastics, and many others, require extremely high levels of sport-specific technique and skill in order to perform well. Many of these sports also involve somewhat unnatural body movements in order to achieve a "good technique." Additionally, in many of these sports, there are a number of elements of a good technique that must be simultaneously performed and which have vastly different and sometimes unnatural movements involving different parts of the body. Many of these movements are not intuitive and can only be perfected by many years of proper instruction (e.g., coaching) and practice. Additionally, in some sports, such as swimming, the immersion of the athlete into a water medium where specific breathing techniques must be mastered makes concentration on practicing good technique much more difficult.

In most sports, the only way for an athlete to know how to improve their technique is to have a coach watch them perform the sport from a distance and then given oral guidance on how to improve their technique. Often coaching guidance is given on how to correct one deficiency in the athlete's technique at a time since the athlete cannot concentrate on multiple deficiencies simultaneously. While this may result in a correction of the deficiency, the athlete's technique in another area may degrade. Therefore, using coaching to improve athletic performance is often very repetitive. Most athletes struggle to understand how to improve their technique even with the best coaching.

The connection between proper technique and performance can be best illustrated with an example related to a specific sport. Consider competitive swimming. It is well known that swimming is one of the most challenging sports to master good technique to perform well.

For example, proper body position in the water is extremely important since this reduces drag. However, proper body position requires the swimmer's head to be lower in the water thereby making breathing more difficult. Proper rotation of the body in some swimming strokes is also very important since this places the body and arms into a position where the swim stroke will be more efficient and effective to obtain more propulsion force. Moreover, a proper body rotation also allows the swimmer to get breaths of air even when the head position is lower in the water. However, rotation performed incorrectly can greatly compromise a swimmer's performance. The force of the arms on the water is important as well. However, the amount of force applied varies greatly during each arm stroke from a minimal force level until the arm and body is in the correct position to provide forward propulsion, to a maximal force when the arm and body are in the correct position for effective force transfer to the water, and then tapering the applied force of the arm to a minimal level as the stroke is being completed. Applying too much force on the water before the arm and hands are in the correct position causes the body position to be degraded so as to increase drag and is a common flaw in even experienced freestyle swimmers. Additionally, there are many other components of good swimming technique including: correct leg position; correct leg kicking movements; proper breathing; proper hip position; and many others.

There are 4 major competitive strokes: freestyle; butterfly; backstroke; and breaststroke. Each of these strokes has significant differences in what qualifies as a good swimming technique and therefore proper technique is specialized to each of the strokes.

Starts and turns are also an important part of competitive swimming. Good starts require a burst of power by the swimmer off of the blocks or pool wall that is followed by a complex aerial movement and water entry that minimizes drag and the reduction in speed so that the swimmer's velocity and momentum are retained, while also ensuring a proper body direction. Then, once the swimmer has entered the water, they often use an undulating motion underwater before breaking the surface of the water. It has been long recognized that the swimmer having the best start of the race can determine outcome among elite swimmers.

Turns in competitive swim races are also very important. Faster turns and the ability to get high velocities off of the wall after each turn can be the determining factor in competition. The swimmer configures their body into what is called a streamlined position so as to reduce drag after each turn. Some turns involve complex underwater summersaults where the swimmer's speed is not reduced as the wall is approached and a maximum force push-off from the water followed by streamlining and dolphin kicking until the swimmer reaches the surface. Other turns have the swimmer touching the walls, followed by a push-off from the wall and streamlining. Starts and turns require enormous practice and are not natural movements.

It is also important to note that swimming is a sport where the swimmer is placed in a medium far different from air. Water is a fluid that by definition cannot sustain a shearing force. While sprint runners on land hardly need to give a thought to the frictional forces between their running shoes and the track surface, swimmers must always place each part of their body into a correct position in the water in order to be able to develop enough forward propulsion force as well as reduce drag to swim effectively, efficiency, and at a maximum velocity. Additionally, most athletes in competitive sports can breath freely. Swimming is a sport where proper breathing techniques are very unnatural and highly restricted.

Traditionally, the methods available for developing good swimming techniques involves several components: extensive practice sessions, sometimes extending to many thousands of yards or meters per day; performing so-called interval training wherein pre-defined sets are performed and repeated (e.g., an set could be to swim freestyle stoke for 100 yards in each interval, repeating the interval 10 times (for a total yardage of 1000 yards) on 1:10 times (i.e., 1 minute and 10 seconds) for each interval; closely observing other swimmers who are known to exhibit good swimming techniques and attempting to emulate their technique; and having coaches at the pool side who can watch the swimmer's technique and give instructions on what the swimmer may be doing wrong and how to improve their technique. Swimmers can also have videos taped of them swimming for later analysis.

The major metric for swimming is the time it takes to complete an interval or a race. Often swimmers in practice use a clock at the poolside as the most important guide to their technique. A faster swim is assumed to translate directly to the ability to perform the swim using a good technique. However, this is not always the case.

The above discussion highlights two important things; the significance of proper technique for good swimming and lower swim times; and the limited resources available to swimmers for helping them develop good swim techniques.

What is needed for athletes to know how to improve their performance is the ability to have real-time feedback on their technique as they perform in any particular sport. This is the focus of the present invention.

SUMMARY OF INVENTION

The present invention is directed to the use of microsensors that are applied to various points on an athletes body during the performance of an athletic activity wherein the microsensors measure and collect data about the athlete's technique and skill during the performance of a sport, analyze this measured microsensor data, and provide the athlete and other interested parties with real-time information that allows the athlete to know how to improve their sports-specific technique, skill and performance.

BRIEF DESCRIPTION OF THE DRAWINGS

FIG. 20 includes Table 1 illustrating microsensor accelerometer parameters suitable for the microsensor module for swimming.

FIG. 21 includes Table 2 illustrating microsensor magnetometer parameters suitable for the microsensor module for swimming.

DETAILED DESCRIPTION OF THE INVENTION

Figure 1:
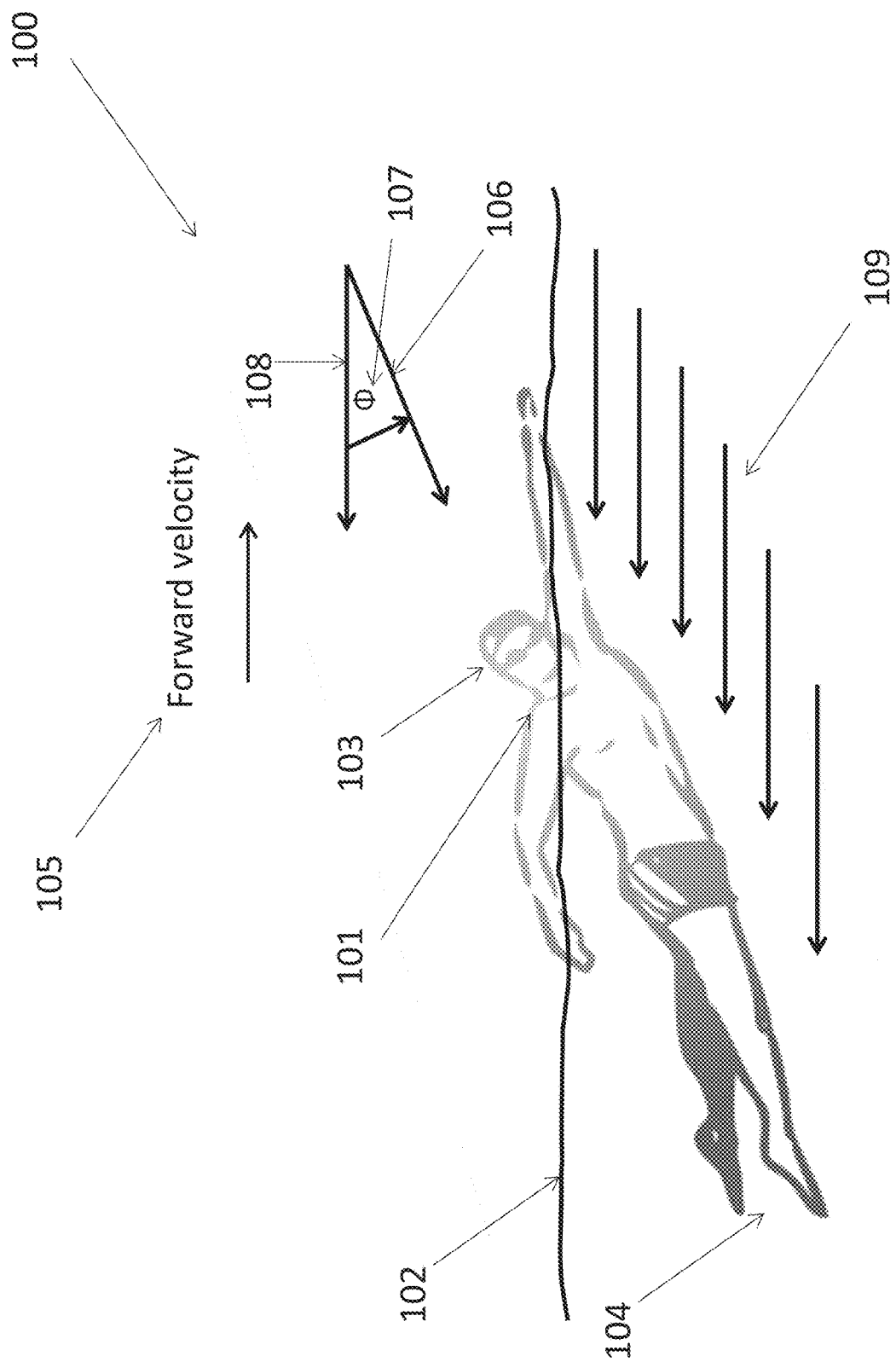
FIG. 1 is an illustration of a swimmer swimming the freestyle stroke and having an incorrect non-horizontal body position in the water.

The present invention is directed to the use of microsensors that are applied to various points on an athletes body during an athletic activity wherein the sensors provide the athletes with real-time useful information that allows the athlete to know how to improve their sports-specific techniques and thereby their performance. As with the background description, the detailed description of the present invention will be focused on swimming as an exemplary example.

It is useful to first provide information of a general nature about the sensor technology employed in the embodiments of the present invention. Recently great advanced have been made in what are commonly called "microsensors" that are fabricated using semiconductor manufacturing technologies. These microsensors are mostly made of silicon, the same material used for integrated circuits. In general microsensors are also commonly referred to as micro-electro-mechanical systems (MEMS) and microsystems. If the features sizes on the die are sufficiently small, these technologies are also referred to as nano-electro-mechanical systems (NEMS) and nanosystems. For brevity, microsensors will be used in the remaining pages of this disclosure and is meant to mean both microsensors and nanosensors.

Microsensors have been implemented for sensing just about every possible physical phenomena including: temperature, velocity, acceleration, pitch and yaw, pressure, force, magnetic field, and many others.

Importantly, these microsensors also have several significant attributes that make them excellent devices for use in monitoring sports techniques. These include: low cost; extremely small size; low power; robust; high reliability; and excellent sensor performance levels.

The present invention uses these microsensors as a means to measure various important body motions and forces in sports in order to provide the athlete with real-time information about specific and measurable attributes of the athletes performance.

The example of swimmer will be used as an illustrative example, first focusing on the most common swimming stroke, the freestyle swim stroke. How to use the present invention for other swim strokes, starts and turns will be described below. Also, how to use the present invention for other types of sports will also be described below.

The freestyle swimming stroke, as sometimes called the front crawl, is the fastest of the swimming stokes. Freestyle is swum in a horizontal position in the water with the body facing downwards. The swimmer's body rolls from side to side while making alternative arm strokes and turning to the side that the arm is currently pulling in the water. The correct head position is a neutral position, facing downwards except during breaths. Breathing is done on one or both sides when the body rotates during the stroke cycles. The arms in freestyle perform alternating movements wherein when one arm is making the stroke underwater while the other arm is performing a recovery action above the water to re-position the arm for a re-entry into the water forward of the swimmer's head.

The arm movements in freestyle are complicated and have been described as consisting of multiple phases including: entry and extension; downsweep; catch; insweep; upsweep; release; and recovery.

The entry and extension is comprised of one hand and arm making an entry into the water with the fingertips entering first followed by the hand and arm. The hand and arm enter the wafer at a slight angle so as to make a smooth penetration of the surface of the water. The arm is fully extended, essentially positioned straight ahead from the shoulder, and with the swimmer reaching as far as possible ahead of the swimmer's head. The swimmer in this part of the swim cycle does not apply any force using this arm for propulsion to the water.

The downsweep is an arm movement wherein the upper arm and elbow remain high in the water moving to outside of the shoulder while the lower arm and hand move downward eventually pointing to the bottom of the pool. Little to no force is applied by this arm and hand onto the water while making the downsweep motion.

The catch is when the forearm and hand are vertical with the fingers pointing to the bottom of the pool. The elbow is high in the water and is called a "high elbow position" or "early vertical forearm (EVF)". The catch is the arm position wherein the arm is put into the best position to be able to apply force against the water to generate propulsion for the swimmer. The catch is the beginning of the propulsive phase of the freestyle stroke.

The insweep is a motion wherein the swimmer moves the forearm arm and hand like a paddle to apply maximum forces against the water. The forearm and hand move as a rigid unit and the upper arm moves backwards and inwards. The hand sweeps from outside of the shoulder to below the abdomen.

The upsweep involves changing the direction of the hand from under the abdomen toward the hip while pushing on the water with the forearm and hand. The swimmer's body rotates to the side so as to move the body away from the hand.

The release is when the arm and hand exit the water. The elbow leads the arm and hand in this part of the stroke.

Recovery is the motion where the arm and hand leave the water at the swimmers hip and proceed through the air to a position in front of the swimmer's head and the fingers re-enter the water.

Importantly, the above description is only for one arm. The other arm and the timing between the two arms are also very important. Specifically, when the swimmer has positioned one arm into a position for maximum propulsion, the other arm is put into a position of maximum extension. This is purposeful. There is a law of physics called the Froude number that asserts that the speed of an object in water is proportional to the square root of the object's length in the water at the same level of propulsive power. Therefore, it is important for the swimmer to be able to obtain this position and timing since it is important to the ability to obtain higher swimming speeds at the same level of effort.

The above descriptions of the different phases of the freestyle stroke provide a very high-level explanation of the major arm and hand movements and therefore are very simplified. The actual body movements are very complex and constantly varying and involve the legs, hips and body core all working in unison with the arms and hands. Nevertheless, it provides the sequence of motions according to phase of the swimming cycle that will be useful when describing the present invention.

Horizontal Position:

Horizontal position of the swimmer's body in the water is one of the most important attributes in good freestyle (and backstroke) swimming technique. If the body is not horizontal it creates enormous drag on the swimmer's body thereby greatly slowing the swimmer's speed and also has a negative impact on many of the other elements of good swimming techniques.

FIG. 1 is an image 100 of a swimmer body 101 with improper body position while swimming the freestyle stroke in water 102. As illustrated in FIG. 1, the swimmer's head 103 is above the water surface 102 and the swimmer's feet 104 are located dimensionally several feet below the water surface 102. As a result, the swimmer's body 101 forward velocity 105 is slowed considerably due to the significant amount of drag forces 109 that the swimmer's body 101 is encountering when swimming in the water 102 with this body position.

The reason why the swimmer's body 101 is encountering significant drag forces 109 is due to the angle of the swimmer's body 101 shown in FIG. 1. The horizontal direction 108 is indicated by an arrow. The angle 107 of the swimmer's body 101 is also indicated by an arrow 106 that is approximately parallel to the swimming's body 101 position in the water 102.

Figure 2:
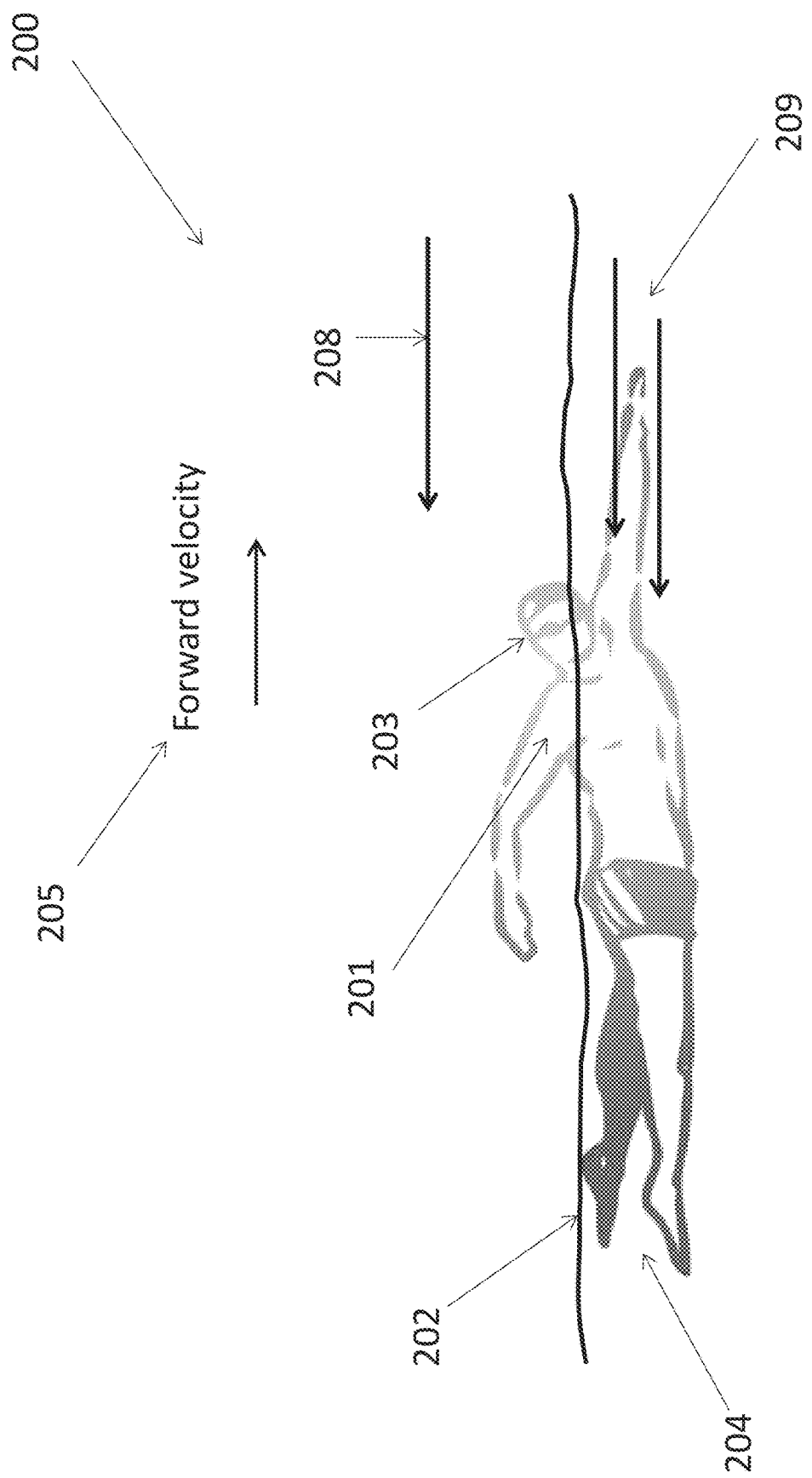
FIG. 2 is an illustration of a swimmer swimming the freestyle stroke and having a correct horizontal body position in the water.

FIG. 2 is an image 200 of a swimmer's body 201 with proper body position while swimming the freestyle stroke in water 202. As shown in FIG. 2, the swimmer's body 201 and head 203 are mostly horizontal and the swimmer's feet 204 are located slightly below the water surface 202. As a result, the swimmer's body 201 forward velocity 205 is not slowed considerably compared to the swimmer's body in 100 due to the reduced amount of drag forces 209 that the swimmer's body 201 is encountering when swimming in the water 202 with the horizontal body position of the body 201.

The reason why the swimmer's body 201 is encountering less drag forces 209 is due to the angle of the swimmer's body 201 that is shown in FIG. 2. The horizontal direction 208 is indicated by an arrow that also is nearly equal to the angle of the swimmer's body 201 in the water 202. That is, they are aligned. The effect of this reduced level of drag forces 209 on the swimmer's body 201 thereby allowing the swimming's body 201 to have a higher velocity for the same amount of propulsive forces and will be able to swim longer and more competitively without tiring as quickly.

It should also be noted that when the swimmer's body 201 position is not proper as shown in FIG. 1, it has a detrimental impact on other parts of the swimmer's stroke technique. For example, the arms will not be able to obtain as effective catch on the water in each swim stroke and the swimmer's body roll will be compromised.

While this importance of being horizontal in the freestyle swimming stroke cannot be overemphasized, this is often one of the most difficult things for beginning swimmers to master since there is large desire for a new swimmer to be able to breathe freely and this is impossible if the body is horizontal since the head will be immersed in the water. Additionally, for males the center of buoyancy is located several inches higher than the center of mass. The result is that male swimmers have to make a conscious effort to keep their legs from sinking below the level of the head.

The swimmer in FIG. 2 can go considerably faster without working as hard based on the enormously reduced hydrodynamic resistance that results from a horizontal swim posture. Microsensors that can be used to measure and monitor the swimmer's horizontal position in the water and provide information in real-time to the swimmer will now be described.

Horizontal Body Position Microsensors:

In one embodiment of the present invention, one or more microsensors are used to provide the swimmer with real-time information about their horizontal body position in the water so that the swimmer has the information to make corrective actions. This capability would be used for the swim strokes wherein a good body position in the water is nearly horizontal, namely the freestyle and backstroke swimming strokes.

One type of microsensor that can be used for measurement of the body position of a swimmer is an inertial microsensor. A one-, two- or three-axes acceleration inertial sensor could be used in the present application. The three-axes accelerator is preferred and has very little additional cost over the one- and two-axes microsensors.

The correct position of the swimmer in the water should be horizontal and should not vary by a significant amount over course of each stroke cycle for both the freestyle and backstroke swimming strokes. Therefore, the sensor can sample at a rate of a few times per second or less and provide a good estimate as the swimmer's horizontal position over time.

Figure 3:
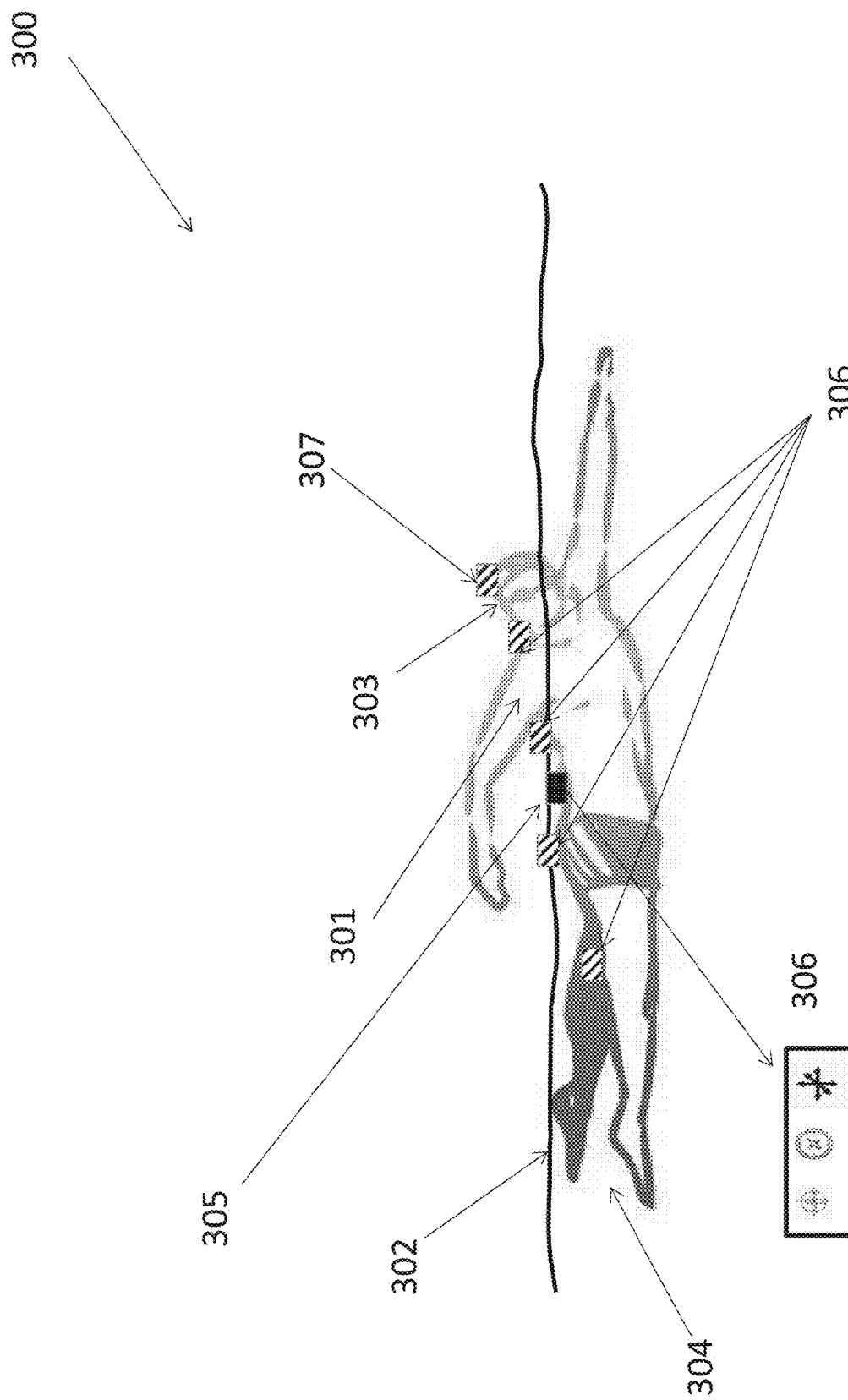
FIG. 3 is an illustration of a swimmer swimming the freestyle stroke with microsensor modules attached to certain parts of the swimmer's body.

An important consideration is where to locate the microsensors on the body. The horizontal body position microsensors and the body roll microsensors (described below) can both be placed on the back of the body since this can be used to detect the swimmer's position in the water and their roll as they proceed through the swim stroke motions. FIG. 3 shows an approximately location of the one or more microsensors. The microsensors are displayed as packaged within a water-proof sensor module package. More or less microsensors can be used depending on how detailed the desired information is as well as cost considerations. As described in this application, a module may include hardware (circuitry, sensors, etc.) and/or software configured to perform operations described herein.

One embodiment 300 of the horizontal body position microsensors in a microsensor module 305 attached to the swimmer's body 301 is shown in FIG. 3. The microsensor module 305 is also shown in an expanded illustration 306 with the various microsensor components. The swimmer 301 is shown swimming the freestyle stroke in water 302. The swimmer's head 303 is shown slightly above the water 302 and slightly turned to the right as the swimmer's body 301 rotates the their right side during the swim stroke cycle to allow the swimmer 301 to take a breath. The swimmer's legs and feet 304 are reasonably well aligned with the swimmer's head 303 and therefore the swimmer's body 301 position is reasonably horizontal as shown in FIG. 3.

A microsensor module 305 is shown attached to the swimmer's 301 back in FIG. 3. The microsensor module 305 can be attached to any position along the body that will be horizontal when the swimmer's body 301 is positioned nearly horizontal, or it can be located at other positions that are not horizontal and calibrated for the difference in angles between the location on the swimmer's body 301 and horizontal to the surface of the water 302. More than one microsensor module 305 and 306 may be used and located along the axis of the swimmer's body 301 in order to provide more information about the swimmer's body 301 position in the water, specifically, how well different points along the length of the swimmer's body 301 line up along a horizontal line.

It is also be useful to place microsensors 307 on the swimmers's 301 head 303 since one of the principal reasons swimmers 301 have bad swim posture and not being horizontal in the water (with the legs 304 sinking) is that the swimmer is lifting their head 303 (either to breathe or see where they are going, or both) while swimming. Lifting of the head 303 from a completely horizontal position causes the lower body (e.g., legs 304) to sink in the water 302 thereby resulting in a non-horizontal body position. This is a very common problem with new swimmers.

The microsensors 307 can detect whether the swimmer's head 303 is in the correct position while swimming and taking breaths. The head 303 is to be turned only slightly to the side to take a breath with one goggle in the water and the other out of the water. A bow wave is created by the swimmer's head 303 that develops a trough at the edge of the mouth that enables the swimmer to take a breath out of the side of their mouths and then turn the head 303 back to a neutral position facing downward.

Figure 4:
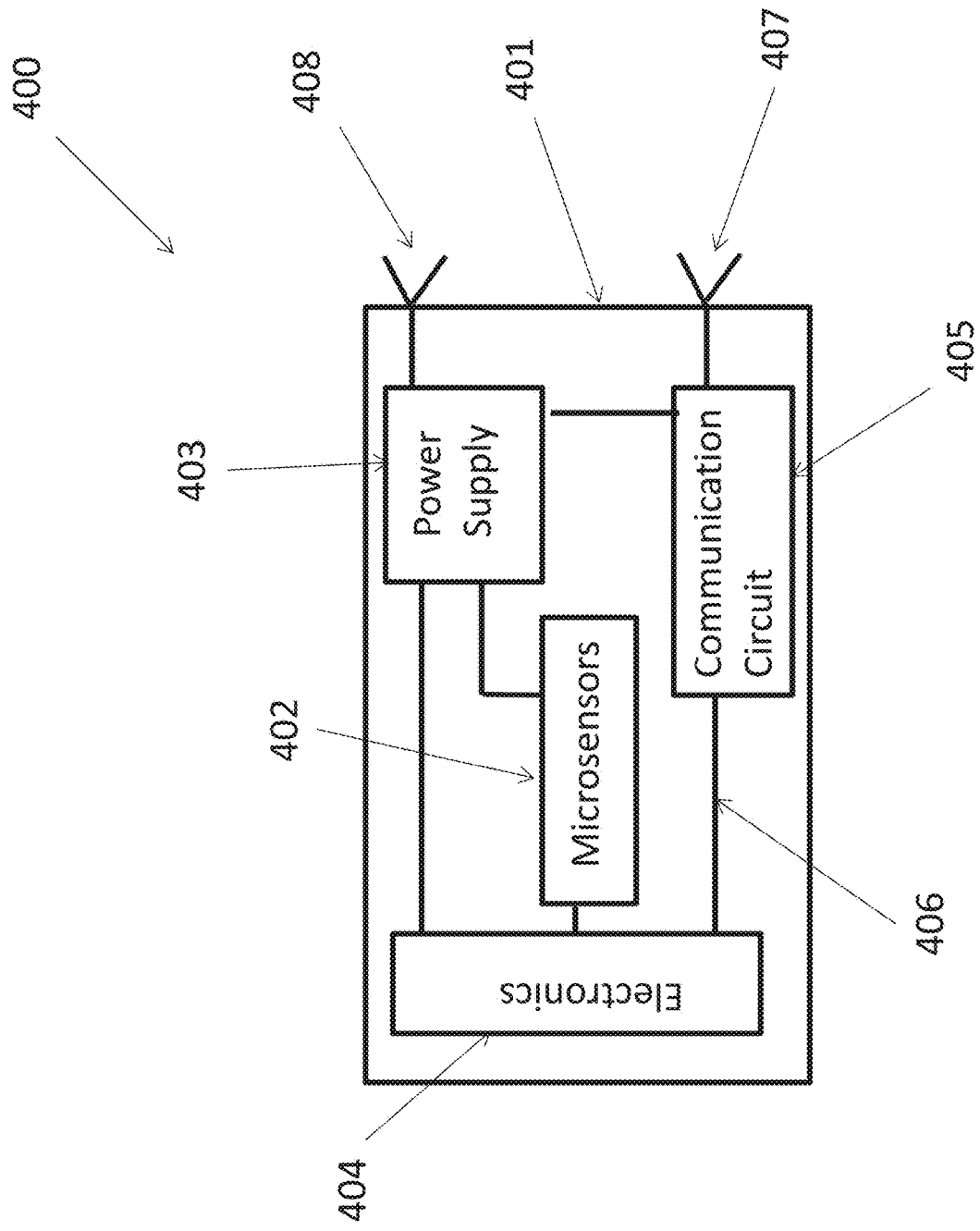
FIG. 4 is a diagram of the interior of a microsensor module showing the various important elements including: microsensors; electronics; power supply; communication circuit; and electrical interconnections.

An embodiment 400 of the microsensor module 401 is shown in FIG. 4. The microsensor module 401 exterior is a water-proof package. The individual microsensors 402 can be soldered onto a printed circuit board, ceramic carrier, or similar, and then packaged in a water-proof container 401. There can be one or more microsensors and microsensors of various types with various sensing modalities within the microsensor module 401 that will be described below. A power supply 403 consisting of a rechargeable battery or similar provides electrical power to the microsensor module 401 components. There are various electronics 404 that are needed to power biasing, signal conditioning, memory, and other electronic and electrical functionality. The electronics 404 may include one or more processors, microchips and/or other processing circuitry configured to perform operations disclosed in this application. In some examples, the electronics may include memory including instructions, which when executed by a processor, control the microsensor module 401 to perform the operations disclosed in this application.

A communications circuit 405 is included to allow the microsensor module 401 to communicate with the external world, that is, to send microsensor readings to the a receiver, as well as allow the user to program certain functions. The communication can be performed using radio frequency or similar as well as using wired connections. The various components are electrically wired 406 together using conductive patterned electrical wiring lines 406 on a printed circuit or ceramic carrier. The microsensor module 401 also includes an electrical jack connection 407 to perform wired communication to the microsensor module 401. An electrical jack connection 408 for re-charging the battery is also provided. The processing of the information is done by examining the sensor output, usually represented as an output voltage signal, but also sometimes as a current, and understanding the relationship between the sensor output and the measurand(s). Any microprocessor or microcontroller can be used for processing the sensor readout data for use by the swimmer or coach.

Figure 5:
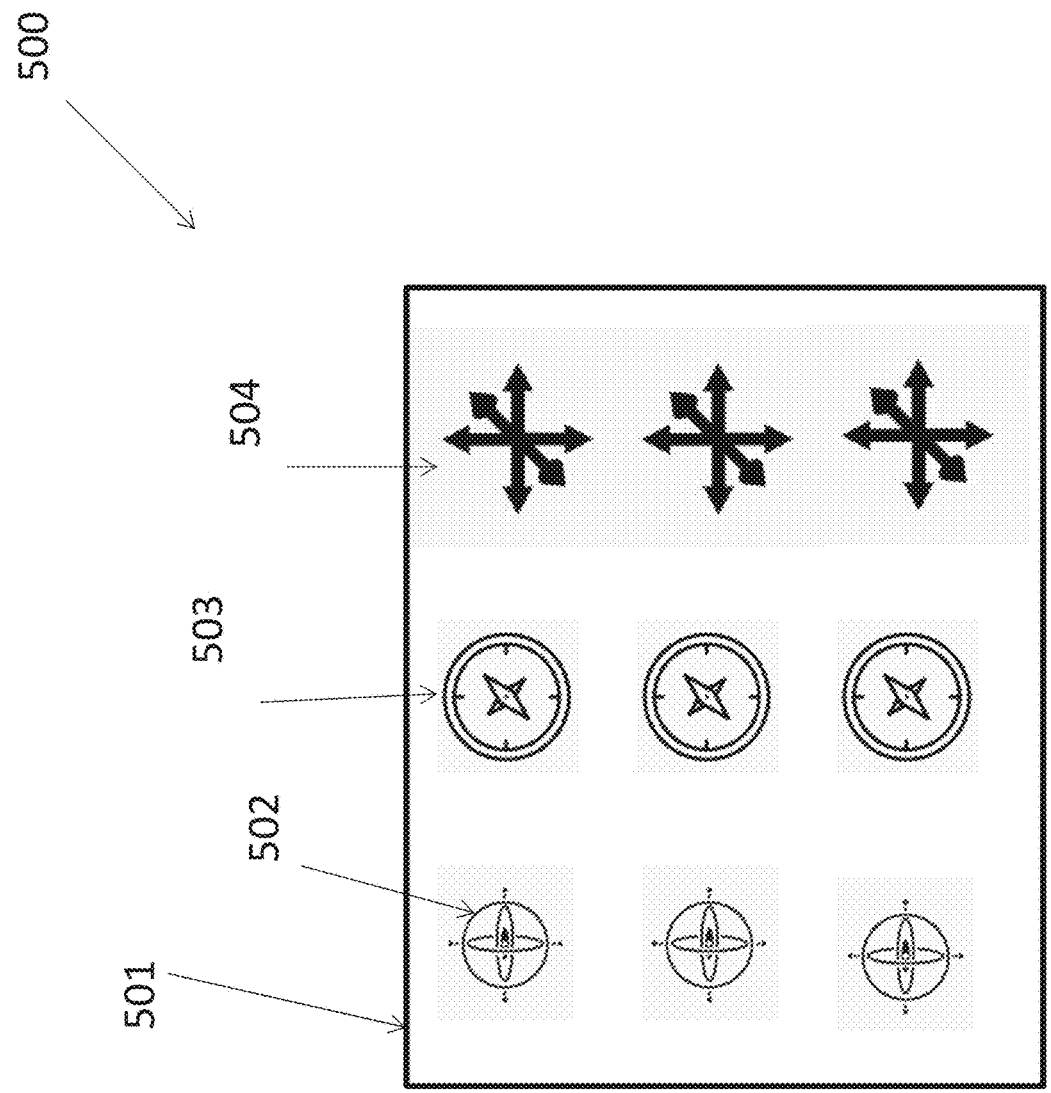
FIG. 5 is an illustration of some of the possible selection of microsensors in the microsensor module.

An embodiment 500 of a microsensor module 401 is shown in FIG. 5. Within it are shown three different types of microsensors: gyroscope microsensors 502; magnetometer microsensors 503; and accelerometer microsesnors 504. The microsensors within the microsensor modules 501 are replicated in order to illustrate that these microsensors are measuring a physical phenomena on the three axis of Cartesian coordinate space: acceleration in the case of the accelerometers 504; the rate of rotation around a particular axis in the case of the gyroscopes 502; and the magnetic field intensity in the case of the magnetometers 503.

It is useful to examine some of the specifications for the individual microsensors.

The dynamic range and resolution of the accelerometer microsensors 504 is a consideration. A dynamic range of +/−35-degrees range is sufficient and the resolution should be better than ½-degree. There are a number of commercially available MEMS acceleration microsensors 504 that have sufficient dynamic range, resolution, low-cost, compact size, and very low power consumption. Some of the current generation of acceleration microsensors 504 is shown in Table 1 (illustrated in FIG. 20).

A sensing range of +/−2 g or better is sufficient for the application, which can be met by all three sensors in Table 1 as well as a number of other acceleration microsensors 504 on the market. For example, one of the horizontal axes will vary from −2 g to +2 g corresponding to +/−90 degree tilt. Since there are 3 axes, +/−90 degree tilt (or roll) can be sensed in all 3 axes independently.

Resolution is given by the least significant bit or LSB of the microsensors. The first acceleration microsensor 504 in Table 1 can sense 0.977 mg change, which corresponds to sin (tilt)=0.977 mg/g which is about ~0.056 degree. Even with noise and error sources are added the sensor resolution will remain well below 0.5 degree.

Raw measurements can be retrieved at rate of 2 kHz. However, typically the highest, reliable data rate for accelerometer microsensors 504 is in the 400-800 Hz range. For the highest data rate is 40-50 Hz. Assuming output data rate of 400 samples/s, the rms sensor noise is given by (~noise density×sqrt (1.11*BW)) for a $2^{nd}$ order, programmable, analog filter with appropriate BW. For the sensors in the table the rms (root mean square) noise is 1.4-2.2 mg. This corresponds to 0.08-0.12 degree in tilt angle.

Although accelerometer microsensors 504 are commercially available as individually packaged; in most cases, co-packaged microsensor combinations are preferred. Since accelerometers 504 and gyroscopes 502 provide local data, their combination with magnetic sensors 503 provides more information at very little additional cost. Magnetometers 503 can be use as a frame of reference since they provide absolute measurements. The microsensors in Table 2 include combinations of accelerometer 504 and magnetometer 503. Gyroscopes 502 are valuable in measuring angular rates and therefore can be useful for measuring the body roll of the swimmer, however this can also be done with accelerometers. The gyroscopes 502 should have low bias drift and the ability to detect rate of angular rotations of a few degrees per second or less.

Notably, most current versions of gyroscopes 502 tend to have significant bias drift, which lowers their value for this application and they also require significant computational resources to counteract error sources. Nevertheless, microsensor gyroscopes 502 as well as all types of microsensors including inertial 504 and magnetometers 503 are all advancing very quickly and therefore the present invention pertains to the use of any of these microsensors.

2). Correct Body Roll Microsensors:

The correct body roll in freestyle (and backstroke) swimming is also very important. If the body does not rotate sufficiently, the swimmer cannot obtain a good catch on the water and thereby cannot obtain the leverage for a strong propulsive stroke. Sufficient body roll is also important for placing the swimmer's mouth into a position to take a breath without lifting of the head and thereby degrading the horizontal body position in the water. However, too much body roll also degrades the ability of a swimmer to get good arm positions for correct stroke technique. An asymmetric body roll wherein the swimmer rotates unevenly from side to side is a common problem with many swimmers breathing on one side. Having an asymmetric body roll is undesirable since it leads to an asymmetric stroke with a resultant slower speed.

Figure 6:
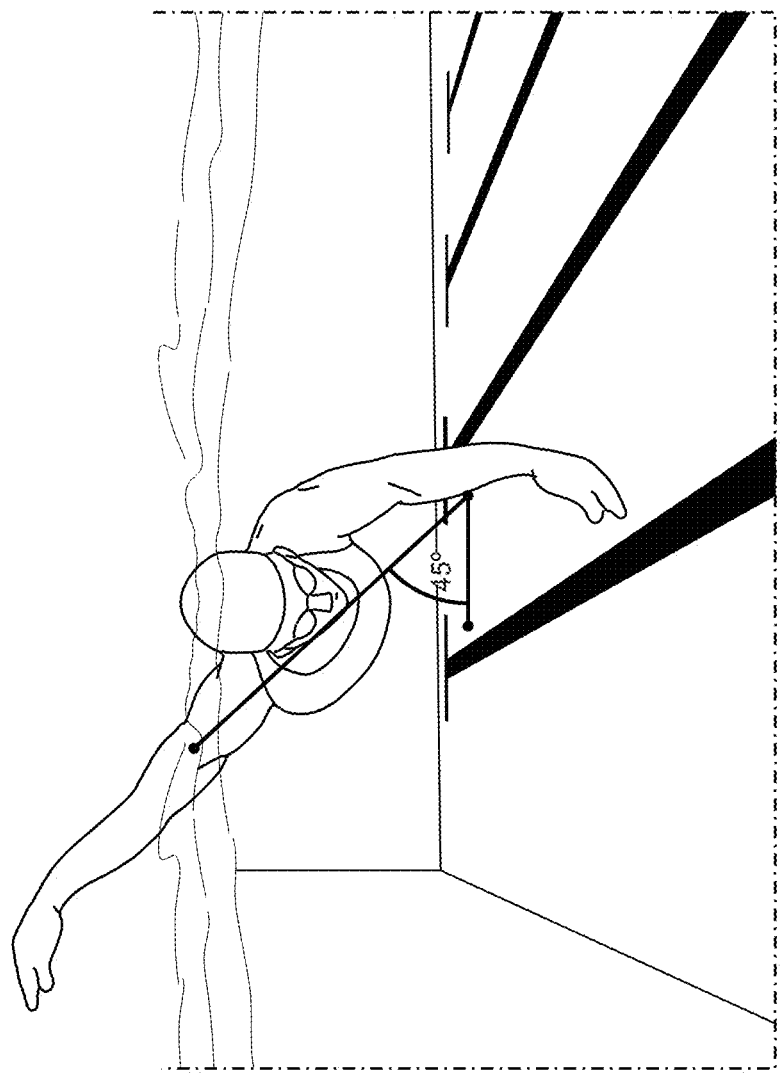
FIG. 6 is a photography showing the body roll of a swimmer having the correct body roll swimming the freestyle stoke.

FIG. 6 is an image of a swimmer with a good body roll. This swimmer has a roll of about 45-degrees, which is considered the correct amount of body roll. The body roll should be nearly equal on both sides.

As shown in FIG. 3, one microsensor 305 or a plurality of microsensors 305, 306 and 307 can be used to measure the swimmer's 301 body roll. While the upper body of the swimmer 301 rotates significantly during the maximum stage of the body roll, the lower body, including the body core (i.e., mid-section of body) undergo a lesser amount of body roll. Therefore, positioning microsensors 305 and 306 along the length of the body, such as described above for the horizontal body position sensors 305, 306 and 307, provides more information about the swimmer's 301 body roll. The body roll sensors 305, 306, and 307 can also be located across the back of the back as well as along the axis of the back.

The body roll microsensors 305, 306, and 307 should have a dynamic range of at least 90-degrees (45-degrees on each side), but 120-degrees may be preferable in order to detect swimmers with excessive body roll. The resolution of the body roll sensor should be between ½ and 1-degree or better.

A complete stroke cycle (includes a full stroke cycle of both arms) occurs in a time of about 1 second.

With regard to sampling rates of the body roll sensors 305, 306, and 307, if it is assumed that a resolution of ½ degree is sufficient, a dynamic range of +/−120-degrees, and a stroke cycle of 1 sec, the sampling rate should be at least 240 samples per second. This number will decrease if the body roll sensor dynamic range is lower, such as +/−90-degrees.

One or more body roll microsensors can be implemented using the same devices used for the horizontal body positioning 502, 503, and 504 shown in FIG. 5, or alternatively, microsensors can be dedicated to measuring the horizontal position of the swimmer and other microsensors dedicated to measuring the swimmer's body roll. In most circumstances it will be preferable to use microsensors to monitor both horizontal body position and body roll.

Figure 7:
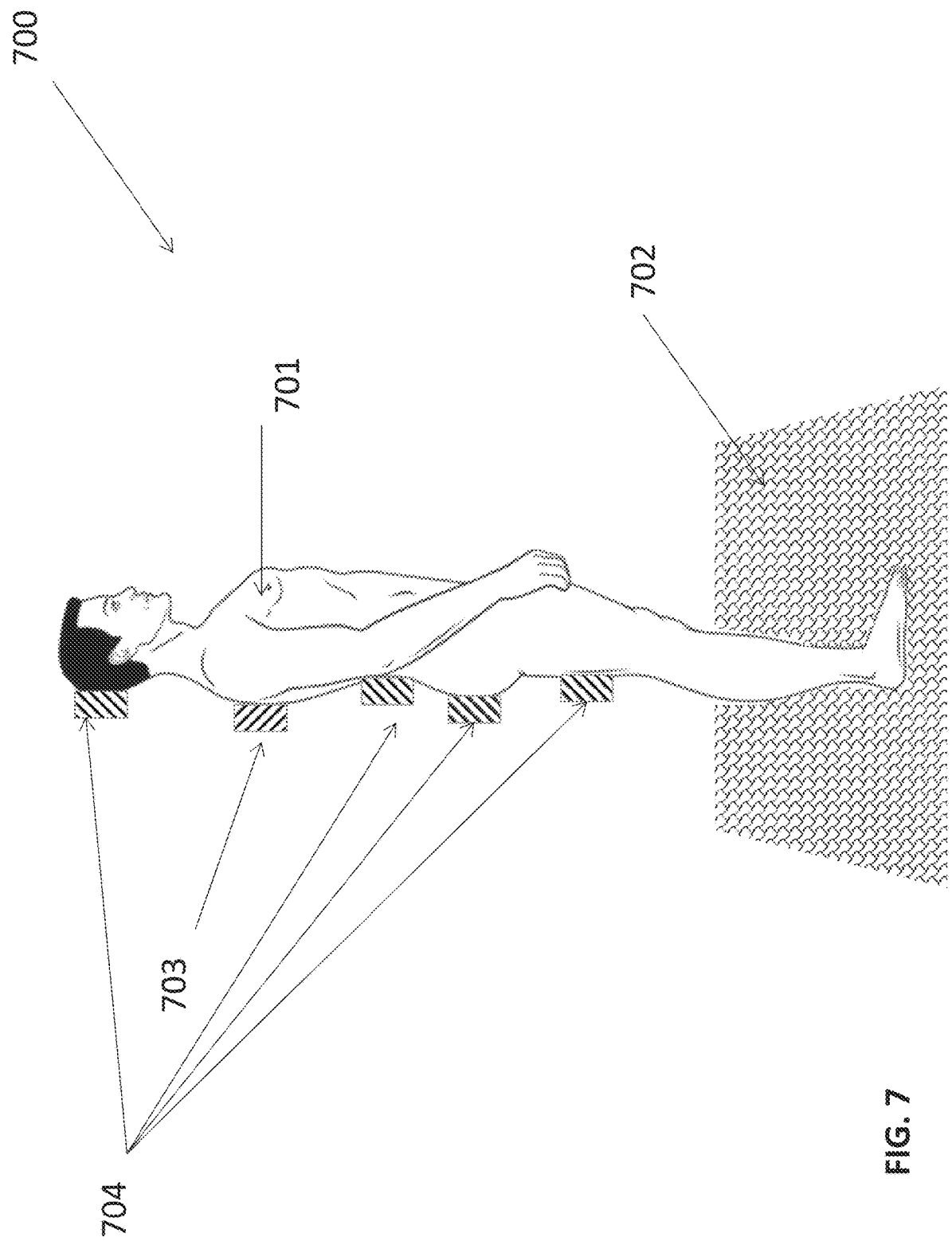
FIG. 7 is an illustration of a swimmer's body standing erect with the microsensor modules attached to the swimmer's body in various locations.

3). Microsensor Positioning:

The positioning of the microsensor modules on the body is an important consideration. One embodiment 700 of emulating the correct horizontal body position can be approximated by the swimmer 701 standing straight on the pool deck 702 as shown in FIG. 7. The swimmer's 701 back should be held straight as possible. The microsensor modules 703 can then be attached to the back of the swimmer 701 while standing in this position and once attached, a microsensor position reading can be taken. This measurement can be used to determine their relative angular position with respect to the gravitational field. Another sensor will be used as a reference parallel to the gravitation field. This calibrating sensor could be integrated into sensor module, an external device such as a level sensor, a cell phone inertial sensor, or any device can also provide this information.

This calibration can be performed on one or all of the microsensors 703 and 704, preferably on all of the microsensors 703 and 704 to be used. Additionally, once the sensors are calibrated to the proper reference, differences in their relative positioning, including relative angular positioning can be performed.

It is noted in FIG. 7 that the microsensor modules 703 and 704 are located on the back of the swimmer, which is preferred in one embodiment. However, the microsensor modules can also be located on the swimmer's front as well. Locating the microsensor modules on the swimmer's front (or back) can also be done for measuring the swimmer's horizontal and body roll in backstroke swimming.

Figure 8:
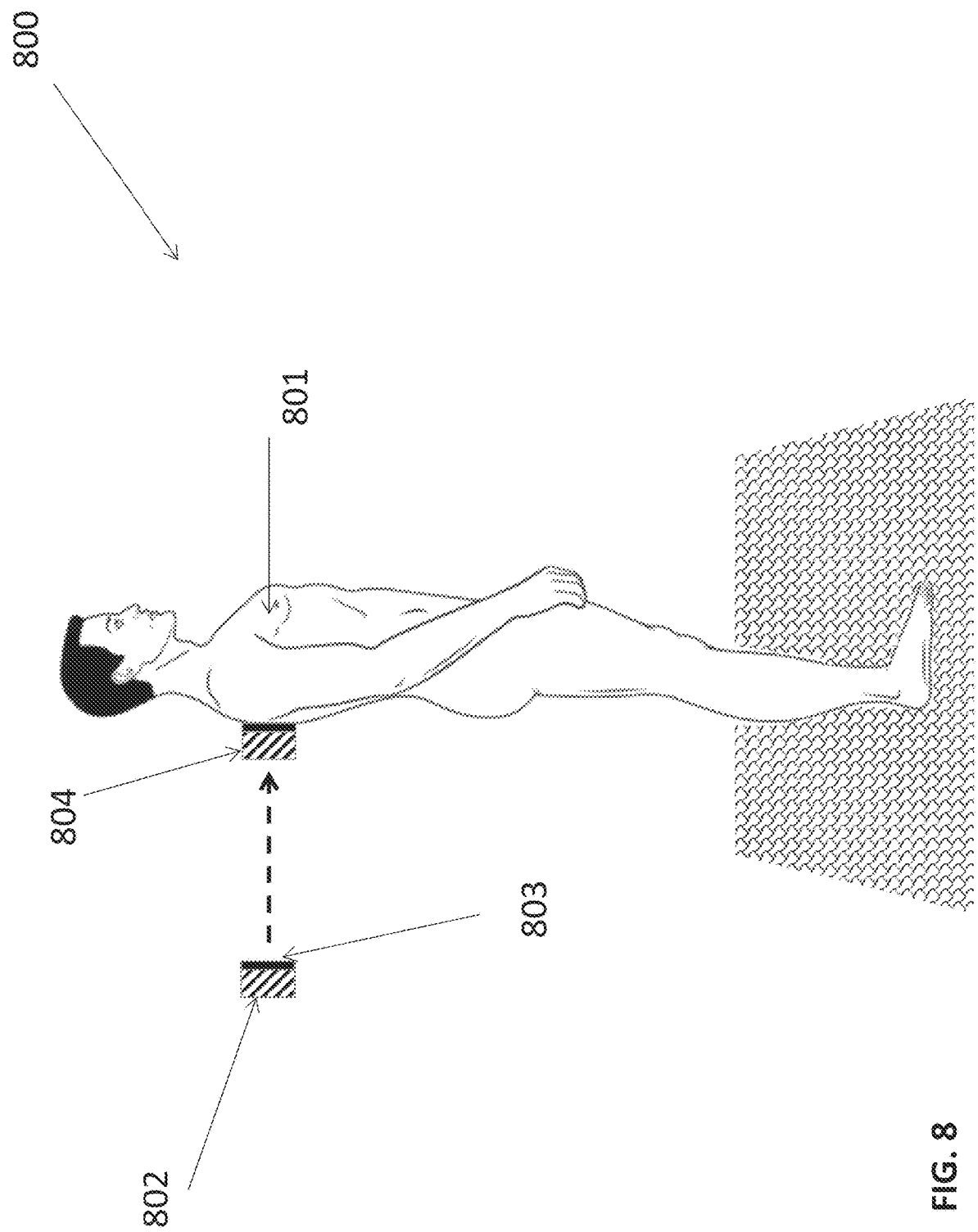
FIG. 8 is an illustration of a swimmer's body standing erect with the microsensor modules attached to the swimmer's body using an adhesive.

4). Microsensor Attachment to Body:

The attachment of the microsensor modules to the swimmer's body 801 is important. In one embodiment 800, the microsensor modules 802 have an adhesive 803 on the surface of the microsensor module 802 that is attached or affixed 804 to the swimmer's body 801 as shown in FIG. 8.

Figure 9:
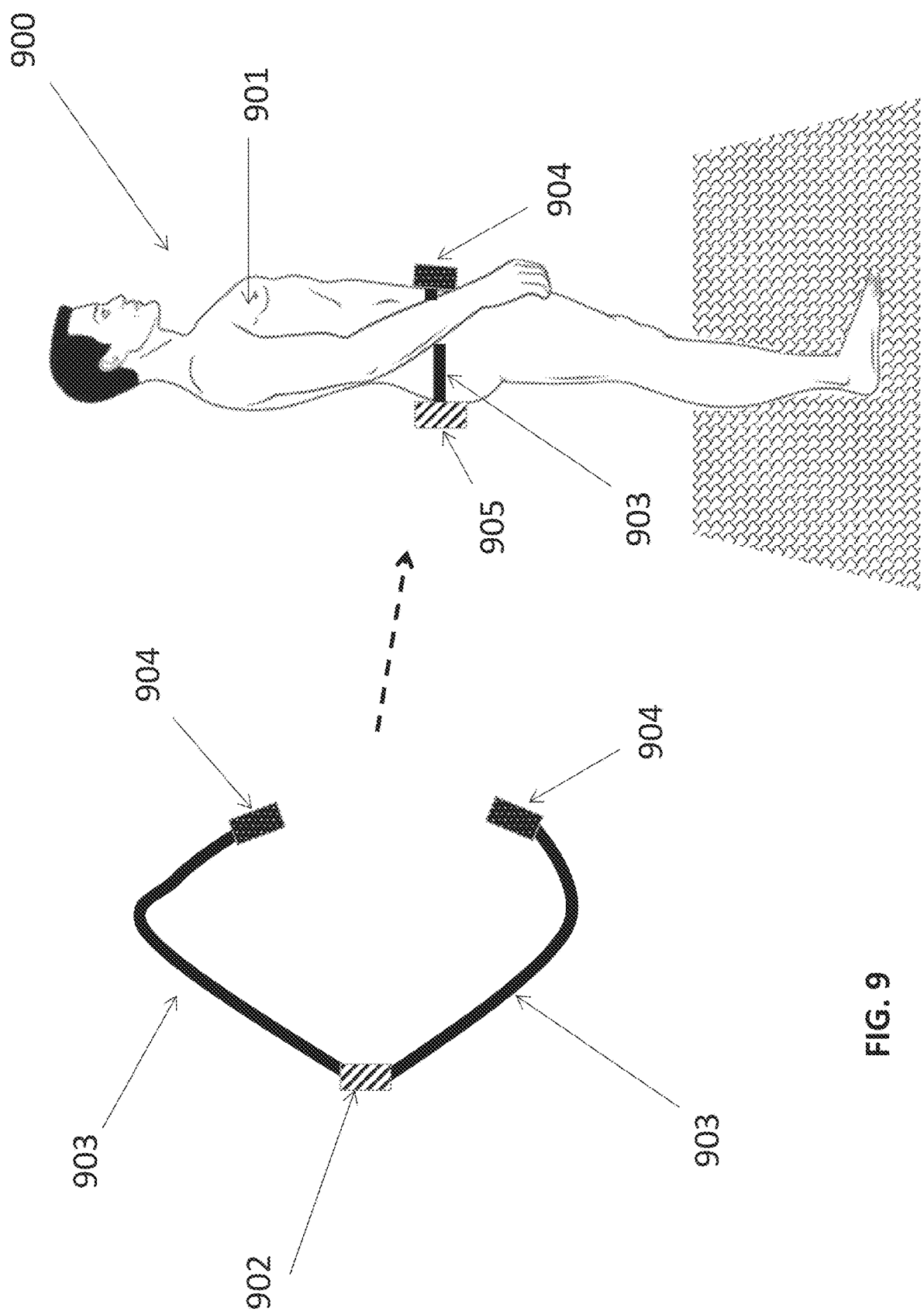
FIG. 9 is an illustration of a swimmer's body standing erect with the microsensor module attached to the swimmer's body using a strap mechanism.

In another embodiment 900 as shown in FIG. 9, the microsensor modules 902 are attached to the swimmer's body 901 using straps 903 that are affixed around the swimmer's body 901 and then clasped together 904 to secure the microsensor modules 902 to the swimmer's body 901.

Figure 10:
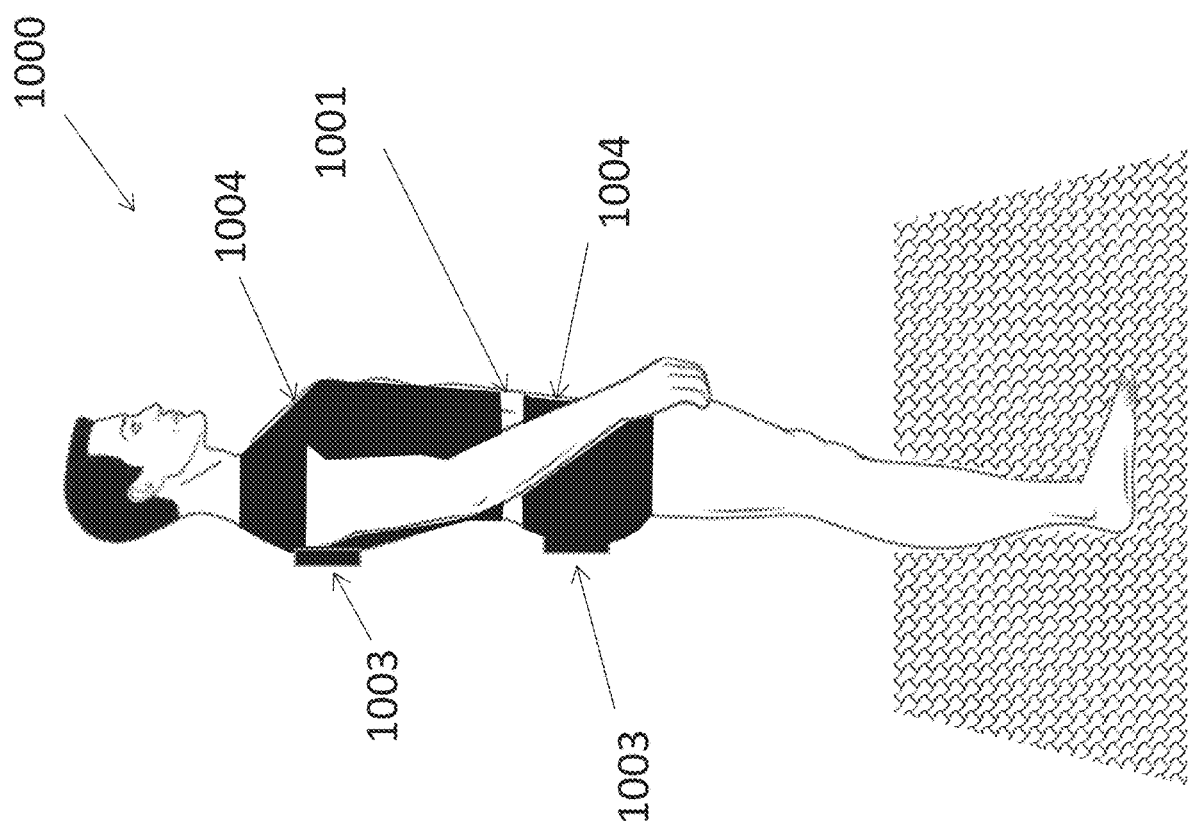
FIG. 10 is an illustration of a swimmer's body standing erect with the microsensor modules woven in the swimmer's swim wear.
Figure 10:
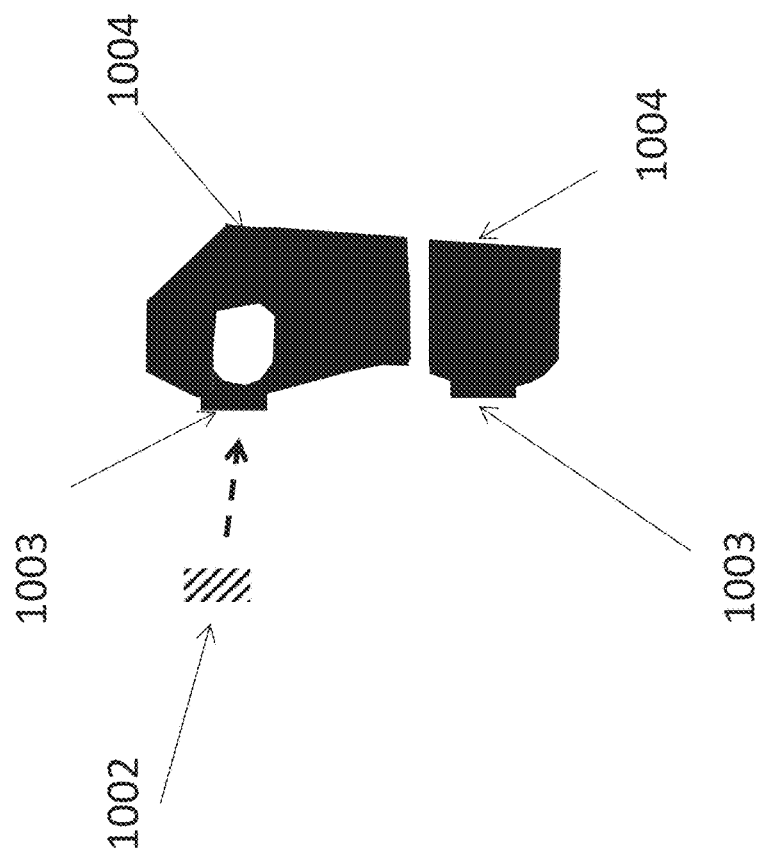

In another embodiment 1000 as shown in FIG. 10, the microsensor modules 1002 are woven 1003 into a fabric 1004 that can be put onto the swimmer's body 1001 as well as used as the swim suit 1004.

5). Communication of the Microsensor Module Information.

Figure 11:
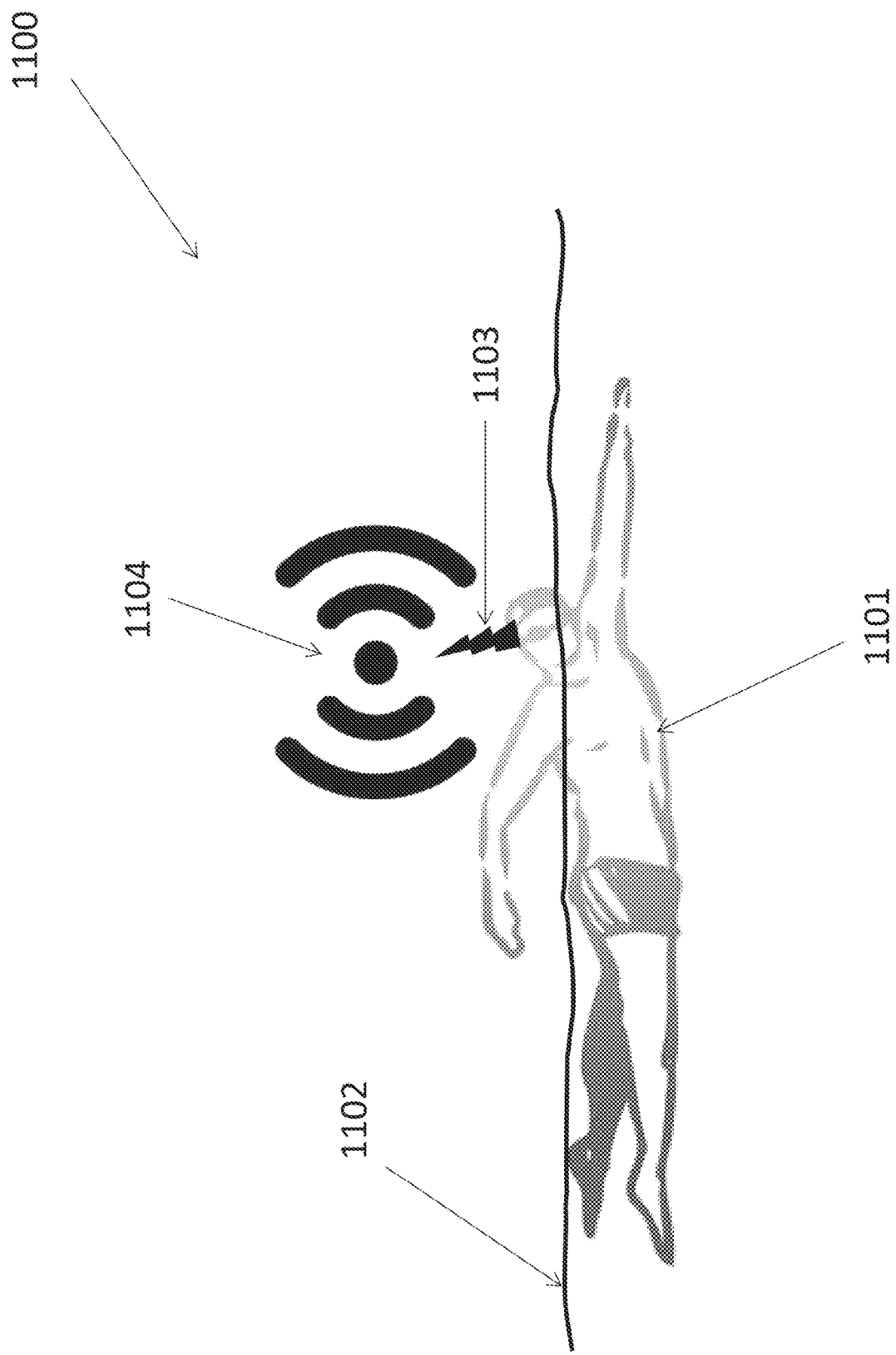
FIG. 11 is an illustration of the swimmer swimming freestyle with a radio frequency antenna that can signal the microsensor module information to other parties on the pool deck.

The information from the microsensors modules can be communicated and processed externally to the swimmer. Any of the known and widely-used communication protocols can be employed such as Bluetooth, WiFi and others, including newer ones that are being introduced in the commercial market. Most radio frequency (RF) signals are blocked when immersed into water. Therefore, the communication circuit can include an antenna that is located on the back of the swimmer or the back of the swimmer's head that protrudes sufficiently out of the water as shown in FIG. 11. In the embodiment 1100 shown in FIG. 11, the swimmer 1101 is shown swimming freestyle stoke in water 1102. An antenna 1103 is placed on the swimmer's 1101 head. This antenna 1103 is connected using a wired connection to the one or more microsensor modules on the swimmer 1101 that communicate the output signal to the antenna 1103. The antenna 1103 propagates a radio frequency signal 1104 that can be detected at the side of the pool. This type of communication system is useful for allowing the coach to be provided with detailed information about the swimmer's technique as well as further processing of the microsensor module data from one or more swimmers.

Figure 12:
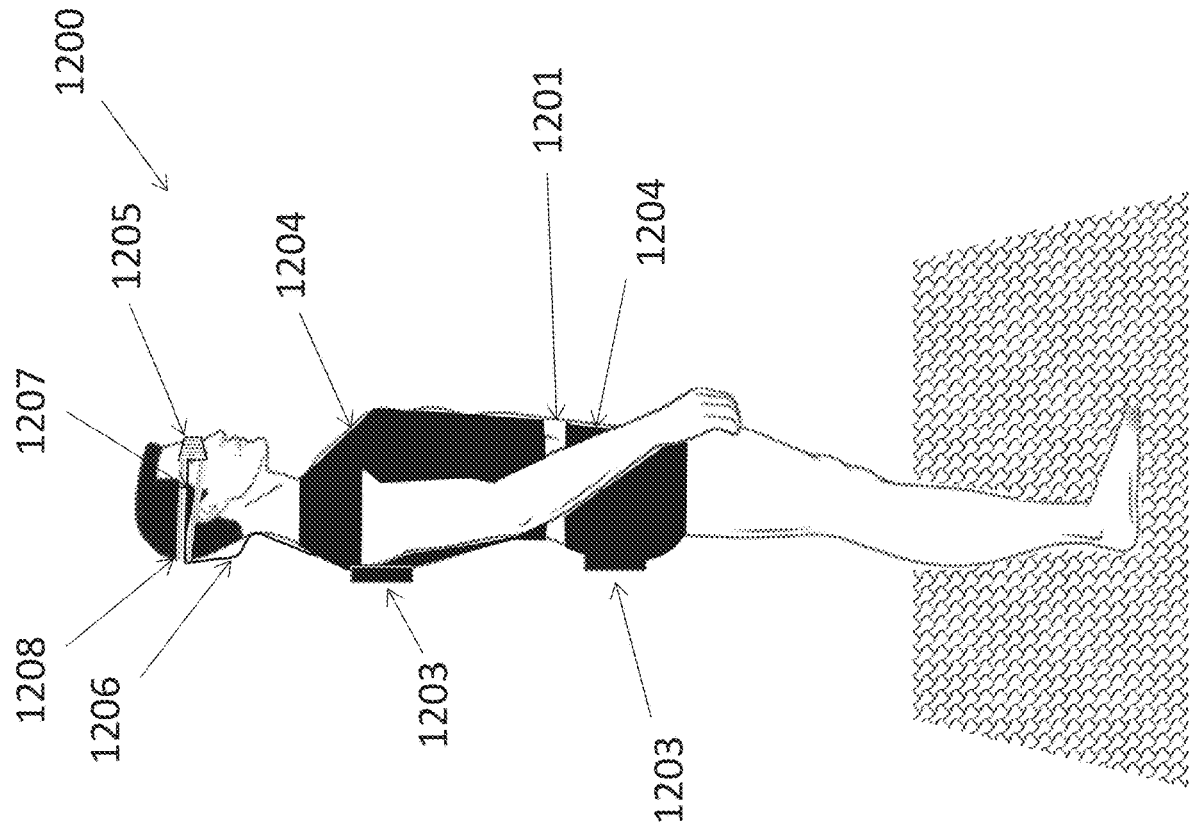
FIG. 12 is an illustration of the swimmer wearing the swim goggles that display real-time information about the swimmer's swim technique to the swimmer.
Figure 12:
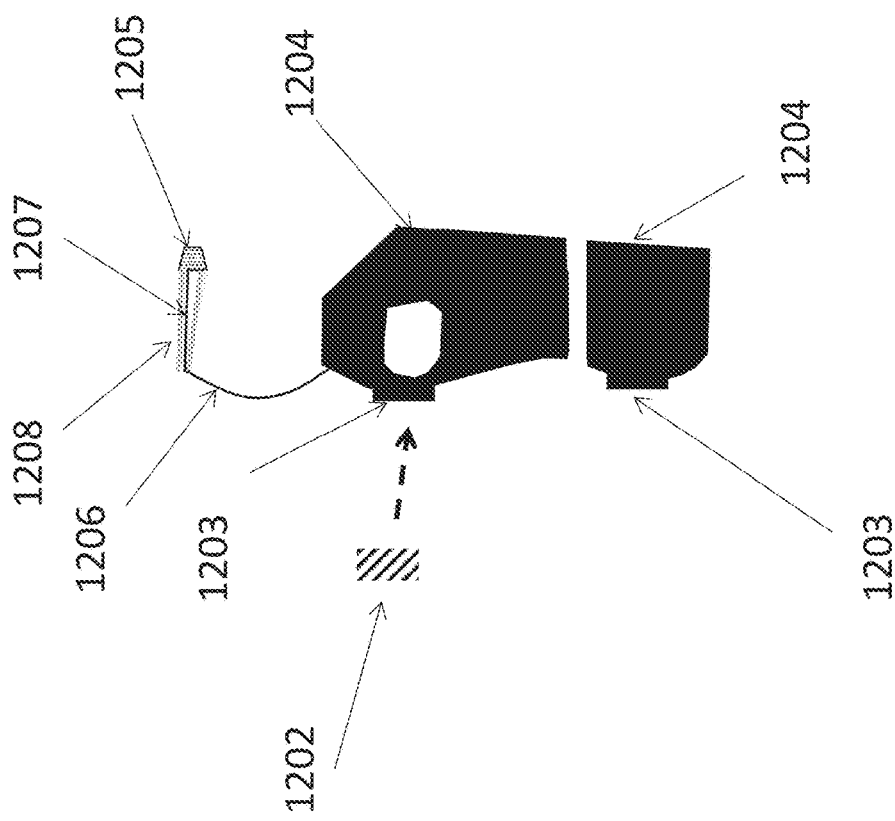

Alternatively, the entire system can be wired together and put onto the swimmers body, including woven into a strap, belt, head cap, and/or the swim clothing that the swimmer can put on before swimming. An embodiment 1200 of this system is shown in FIG. 12. The swimmer 1201 has a swim suit 1204 that has the microsensor modules 1202 woven into or attached to the fabric of the swim suit 1204 so as to make the microsensor modules embedded 1203 into the swim suit 1204. There is electrical wiring 1206 embedded into the swim suit 1204 to connect the microsensor modules 1203 together and connect the microsensor modules 1203 to the swimmer's 1201 goggles 1205. The goggles are attached to the swimmer's head 1201 using straps 1208 to secure the goggles 1205 to the swimmer's face 1201. There is an electrical wire 1207 running along the straps 1208 to connect the microsensor modules 1203 to the goggles 1205. This avoids the problems of propagating the radio frequency signals from the swimmer in the water to poolside.

6). Providing Swimmer with Real-Time Microsensor Module Information.

The most effective method to provide feedback about the swimmer's technique is to instrument the swimmer's goggles with an electronic display. The swimmer's eyes are constantly focused on the eyepieces of the goggles and therefore will always have sight of information if it can be displayed there. One embodiment is to project an image onto the goggle inner surfaces that is a numerical or symbolic representation of the swimmer's technique.

Figure 13:
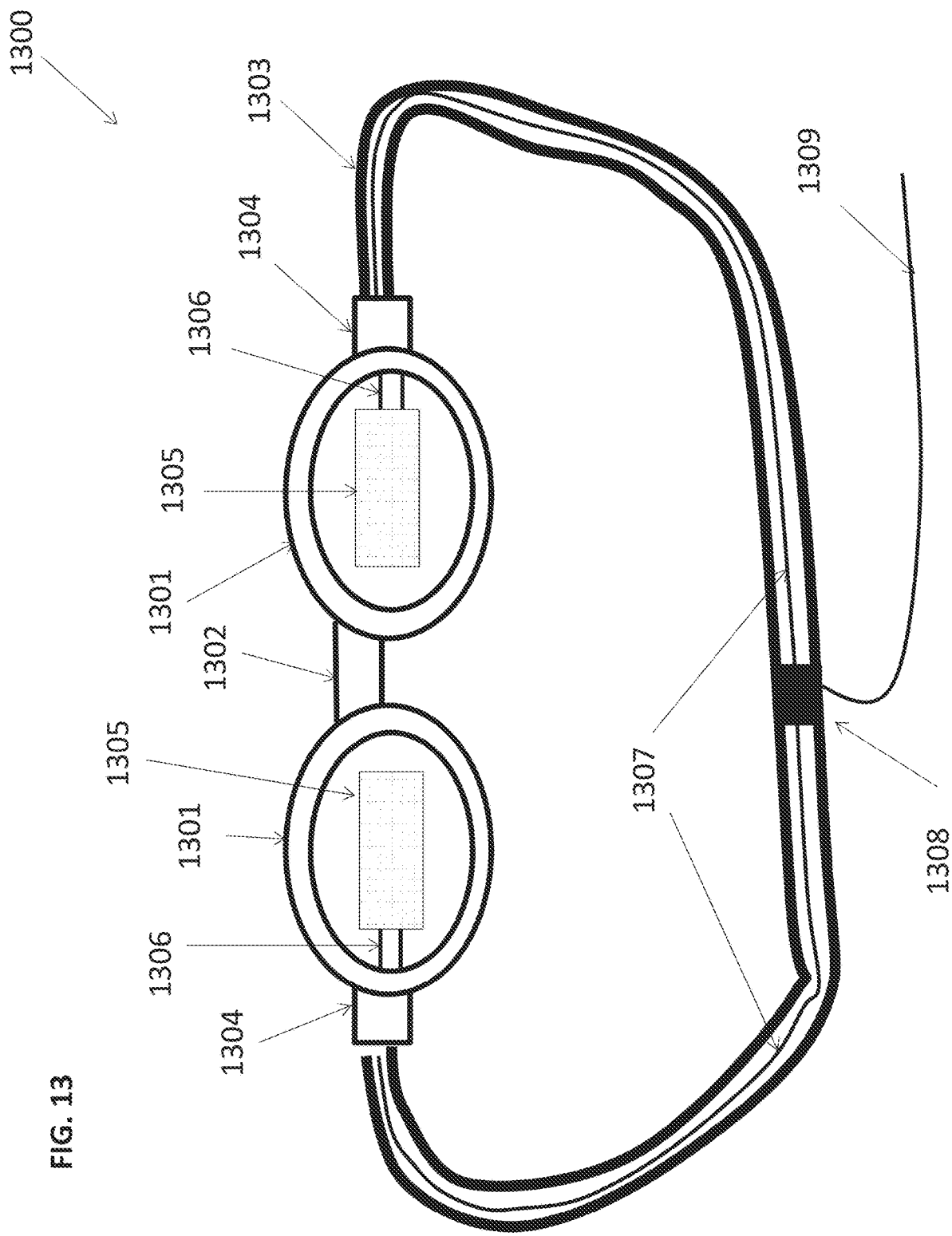
FIG. 13 is an illustration of the swim goggles that display the real-time information about the swimmer's swim technique to the swimmer in the eyepiece of the goggles.

An example embodiment to display the information to the swimmer in real-time is shown in FIG. 13. A pair of goggles 1300 is shown in the embodiment and goggles are routinely worn by swimmers. The goggles have eyepieces 1301 that allow the swimmer to see in the water and that seal around the swimmer's eyes so as to make them water proof. The goggles 1300 have an adjustable nose-bridge 1302 element to obtain a better seal around the swimmer's eyes. Flexible straps 1303 are used to secure the goggles 1300 to the swimmer's face around the swimmer's head. The straps 1303 are adjustable. There is a optical driver circuit embedded in a water proof module 1304 attached to the sides of the goggles 1300, that are electrically connected 1306 to a partially transparent display 1305. The optical driver module 1304 is connected to an electrical wiring 1307 that is attached or embedded into the goggle 1300 straps 1303. The wiring 1307 terminates to an electrical connector 1308 that is connected to an electrical wire 1309 that connects to the microsensor modules or an anteanna. In some examples, the optical driver module may include circuitry configured to wirelessly connect to one or more of the microsensor modules. In some examples, one or more of the microsensor modules may be connected to and/or included as part of the goggles 1300. For example, a microsensor module may be positioned on one of the eyepieces, between the eyepieces (e.g., strap between the eyepieces), on a strap adjacent to a side of the athletes head and/or on a strap on a back of the athletes head to provide an indication of the positioning of the athletes head while performing the sport. In some examples, an antenna for communicating with the microsensor modules may be provided in the straps 1303.

6). Information Displayed to Swimmer.

Figure 14:
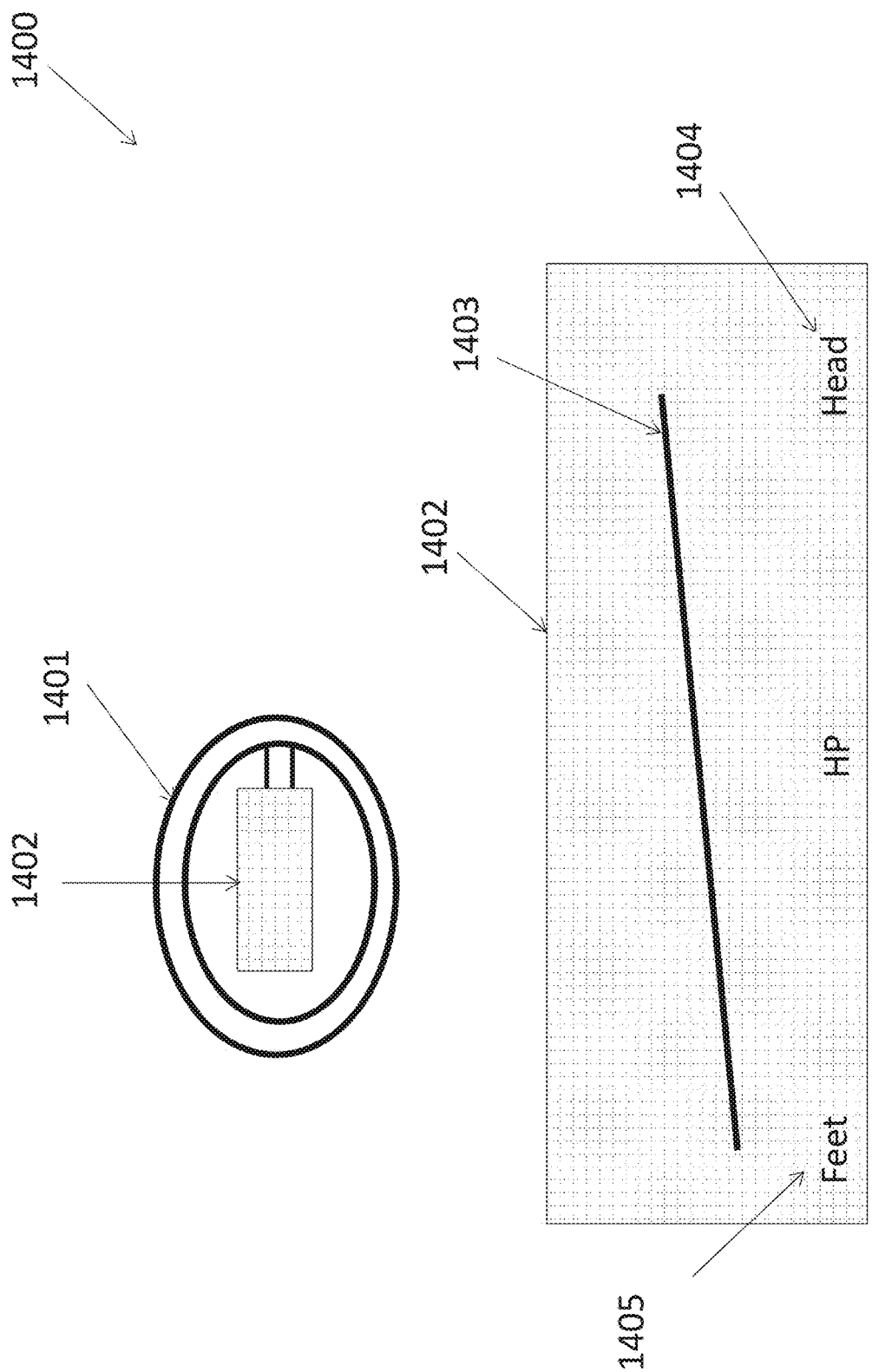
FIG. 14 is an illustration of the display of the swimmer's horizontal position in the water when swimming freestyle or backstroke swimming stokes.

The information provided to the swimmer must be straightforward and simple since there is not sufficient space on the display inside the goggles to provide extensive information. An embodiment 1400 of a display of the information to the swimmer is shown in FIG. 14. The electronic display 1402 inside the goggle 1401 eyepiece is shown in expanded form at the bottom. The display 1402 has a line 1403 that represents how horizontal the swimmer's body position is in the water based on the microsensor module information. If the line 1403 is perfectly horizontal, then the swimmer's body is horizontal. If the line 1403 is tilted, the swimmer is not horizontal in the water. The display 1402 has one side representing the swimmer's head position 1404 and the other side representing the position of the swimmer's feet 1405 relative to the swimmer's head 1404. The swimmer can see a representation of their body position on this display 1402 and quickly determine that an adjustment is needed to become more horizontal and therefore more hydrodynamic efficient in the water.

Figure 15:
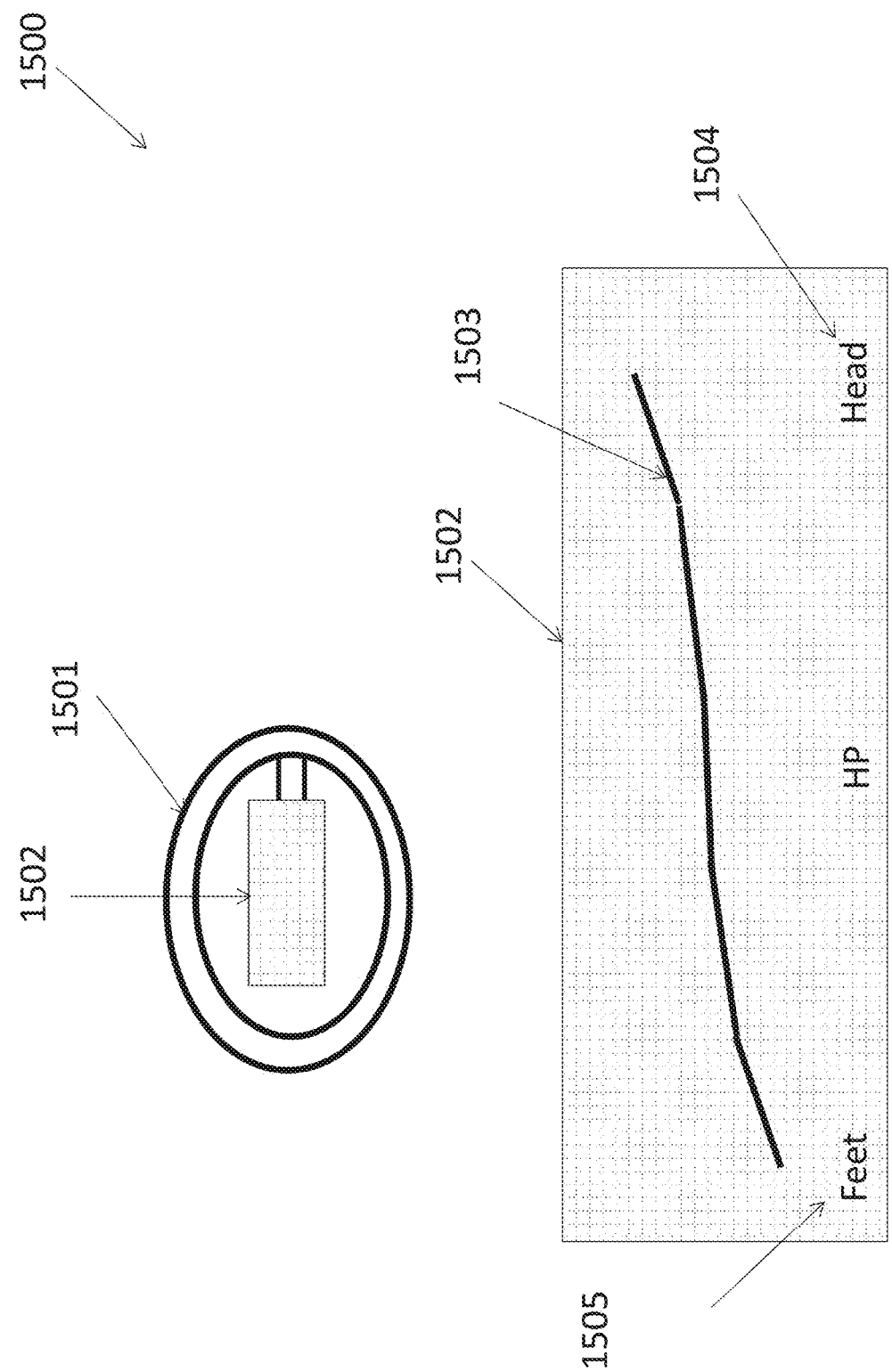
FIG. 15 is an illustration of the display of the swimmer's horizontal position in the water when swimming freestyle or backstroke swimming stokes when using a multiplicity of microsensor modules along the length of the swimmer's body in order to provide a more detail representation of the swimmer's profile in the water along different portions of the swimmer's body.

In an alternative embodiment 1500 shown in FIG. 15, a multiplicity of microsensor modules along the length of the swimmer's body provides a more detailed presentation of the swimmer's body position in the water along the swimmer's body length. The electronic display 1502 is located in the goggle eyepiece 1501 and presents a line joining each sensor reading on each end to create a continuous line 1503 along the swimmer's body. The swimmer's feet 1505 are clearly dropping more than other parts of the swimmer's body. This may be an indication that the swimmer's feet 1505 are not sufficiently kicking to uplift the swimmer's legs and feet 1505 in the water and the swimmer's head 1503 may be raised too high in the water causing the legs and feet 1505 to sink. The display 1502 indicates that the swimmer's head 1503 is high and therefore if the swimmer positions their head 1503 into the water, this may solve the problem and cause the swimmer's body to obtain a more horizontal body position.

The display of horizontal body position can be used for both freestyle and backstroke swimming strokes.

Figure 16:
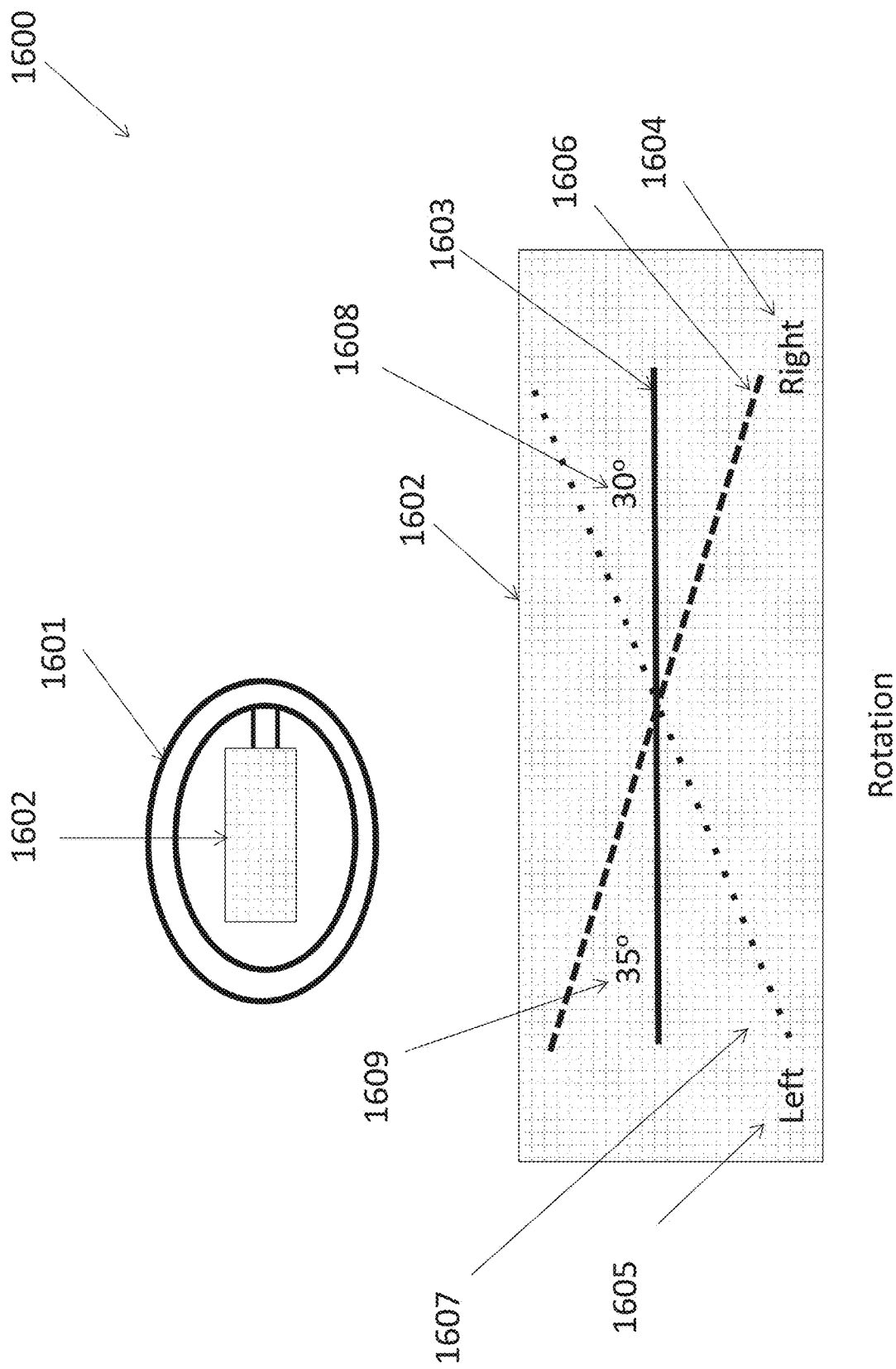
FIG. 16 is an illustration of the display of the swimmer's body roll in the wafer as the swimmer is swimming freestyle or backstroke swimming strokes.

An embodiment 1600 to display the rotation of the swimmer's body is shown in FIG. 16. The information about the swimmer's body rotation is measured by the microsensor modules. The information is provided on a display 1602 within the swimmer's goggle eyepiece 1601. In the expanded view at the bottom, the electronic display 1602 shows the swimmer's right 1604 and left 1605. A horizontal line 1603 is provided as a reference. A dotted line 1606 represents the swimmer's rotation on the right side during each stroke cycle and a different dotted line 1607 represents the swimmer's rotation on the left side during each stroke cycle. Angular measurements for the right 1608 and left sides 1609 are also provided since it can be hard for the swimmer to discern the exact angle of rotation from just the angle of the lines.

While the horizontal body position and body rotation microsensor modules have use for the freestyle and backstroke swimming strokes, they also can be useful for breaststroke and the butterfly stroke. The body positions in the water for both breaststroke and butterfly are not horizontal, but instead undulate in a cyclical fashion. Nevertheless, microsensors modules attached to the body can have a sampling rate wherein the microsensors can take measurements at discrete times during each stroke cycle and use this information to provide the swimmer with feedback as to correctness of their undulation technique. For example, the body has a non-horizontal position throughout most of the stoke cycle in these swimming stokes and these can be detected and measured with sufficient accuracy using microsensor modules placed along the length of the swimmer's body from head to feet. That is, the microsesnor modules can be used to measure the amount of angular position of each part of the body during execution of these strokes and provide information about the quality of the swimmer's swim technique.

Other microsensors for additional information.

The motions of the arms and legs during execution of the strokes in swimming are also very important to the swimmer's technique. The arm motions are extremely complicated in 3-dimensions. In freestyle, arm entry should be at a slight angle to the surface of the water with the fingers entering first. The arm extends forward above the head until the body has rolled the maximum amount on that side, whereupon, the arm is then bent at the elbow so as to point the lower arm and hand towards the bottom of the pool. This is called the downsweep portion of the swim cycle. Little to no downward pressure should be placed on the water by the swimmer since this only pushes the swimmer's body upwards thereby creating increased drag. Once the lower arm and hand are pointed approximately at the bottom of the pool with the arm nearly orthogonal to the pool bottom, the swimmer then is at the catch phase of the swim stroke. This arm position is also sometimes referred to as a high elbow position or an early vertical forearm position. This initiates the propulsive part of the freestyle swim stroke. At this point, the swimmer pulls backwards using the forearm similarly to a paddle to pull the swimmer through the water. The arm motion accelerates through this motion until the hand reaches the waist and thigh whereupon the force on the water is relaxed as the swimmer's hand begins to exit the water. The arm is then rotated in the air above the swimmer's body and then re-enters the water for the start of another swim stroke.

The motions of the legs are less complicated, but are important since incorrect leg motion can significantly degrade other aspects of the swimmer's stoke technique. Incorrect leg motions will create significant drag on the swimmer thereby slowing the swimmer's forward speed.

The legs can undergo either a two-, four- or six-beat kicking pattern wherein this describes the number of kicking cycles for each arm stroke. The six-beat pattern when performed correctly increases the swimmer's forward propulsion, but it also consumes considerable energy to execute. As a consequence, swimmer's tend to use kicking patterns with higher beats for swimmer short distances and lower kick beat counts for longer distance swims. Some swimmers are capable to changing their kicking patterns during a swim in order to increase their propulsion while also conserving energy. In general, the correct kicking pattern has very little bending at the knee and the motions of the feet are described as a flutter kick. That is the foot is vigorously cycled at the angle so as to create a bending motion in the foot that maximizes its force level on the water in the backward direction.

These complicated arm and leg movements can be measured using inertial sensors located at multiple points along the arms and legs, including the hands and feet. The number of sensors will preferably increase as the distance from the swimmer's core increases since the movements tend to become more complex at the more extended regions of the arms and legs. Since the legs are submerged in water and the arms spend considerable time underwater, the sensors will need to be wired together and connected to a processing and communication circuit. As before, the sensors can be attached to the swimmer's body using straps, belts, as well as woven into a fabric that the swimmer can put on their body.

Figure 17:
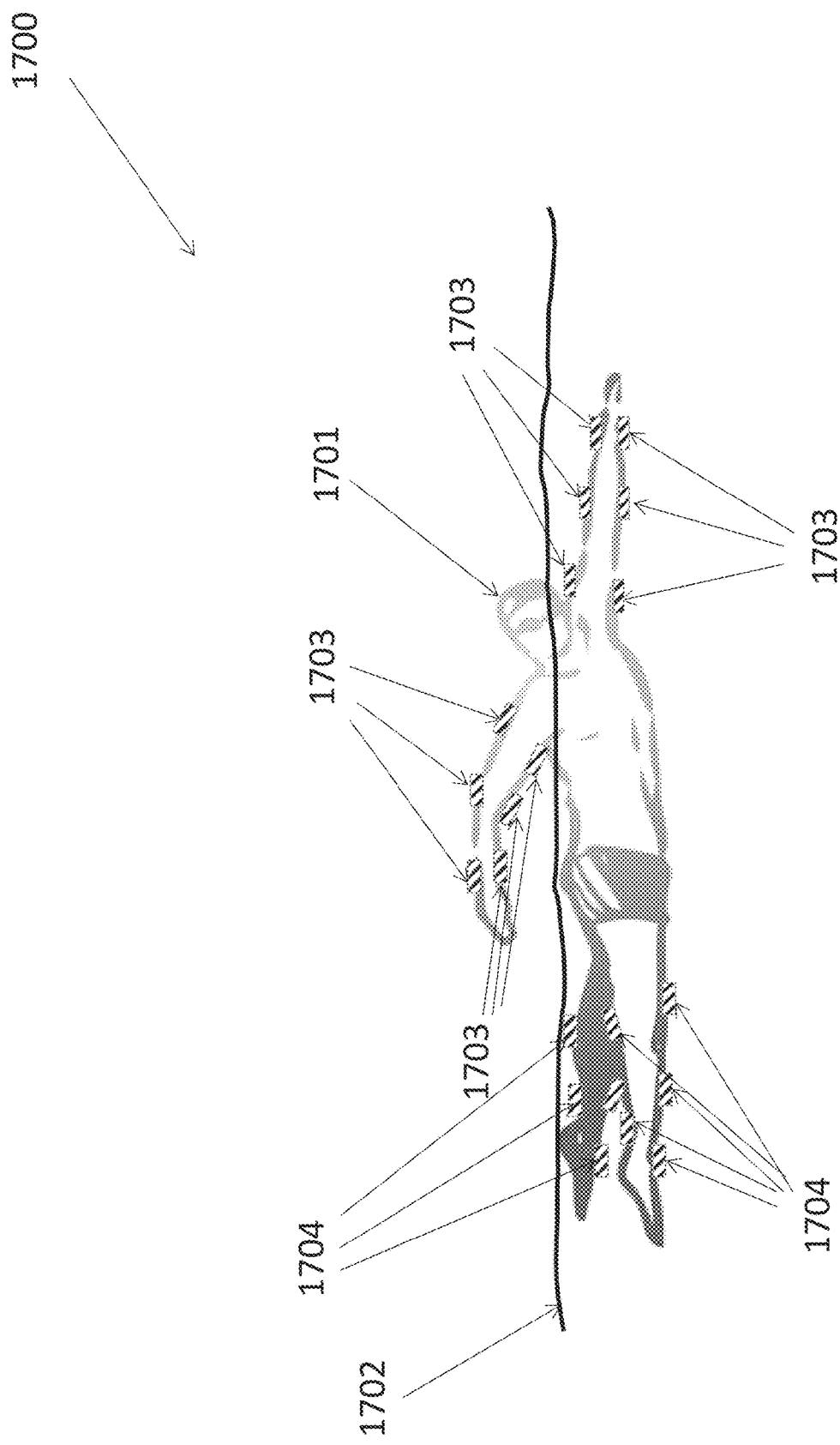
FIG. 17 is an illustration of a multiplicity of microsensor modules placed on the arms, hands, legs and feet of the swimmer in order to measure the 3-dimensional motions and forces of the swimmer while swimming.

An embodiment 1700 of microsensor modules placed on a swimmer's body 1701 in the water 1702 swimming freestyle is shown in FIG. 17. A number of microsensor modules 1703 are placed on the swimmer's 1701 arms and hands in various positions along the length of the arms and hands to measure their motions in 3-dimensional space. Additionally, a number of microsensor modules 1704 are placed on the swimmer's 1701 legs and feet in various positions along their length to measure their motions in 3-dimensional space. The information measured by these microsensor modules can be used to make various measurements about the motions of the arms, hands, legs and feet during swimming and make determinations as what is correct and not correct in the swimmer's 1701 swimming technique. The microsensors modules 1703 and 1704 are used to measure velocity, acceleration, and angular rate of change of the various body parts during the execution of the swimming strokes. The microsensor modules on the arms and legs can be used as shown in FIG. 17 for the freestyle technique and can also be used for the backstroke, breaststroke and butterfly techniques. They can also be used in drills performed by the swimmer 1701 during swim practices.

The combination of the body position microsensor modules and the arms, hands, legs and feet 3-dimensional motion microsensors is a preferred embodiment since the body position in the water has an effect of the ability of the swimmer to execute proper technique in the arms, hands, legs and feet, and vice versa.

The evaluation of the arm and leg motions has been focused only on their motions in 3-dimensional space. It may also be important to monitor the amount of force that the swimmer places onto the water when executing swim strokes. Also, it is important to monitor when the force is applied to ensure that the arm is in the correct position before applying force for propulsion. As noted above, the forearm and hand of the swimmer during the insweep phase of the stroke is where the most force is applied during the freestyle stoke. Therefore, microsensors to measure forces on these surfaces of the swimmer's 1701, arms, hands, legs and feet can be used to determine the amount of force that the swimmer 1701 places onto the water at various parts of the swimming stroke cycle. Pressure sensors can be used as force sensors wherein the force is the measure applied pressure multiplied by the area of the sensing element of the pressure sensor. The pressure sensors can be placed onto the arms, hands, legs and feet as shown in embodiment 1700.

Figure 18:
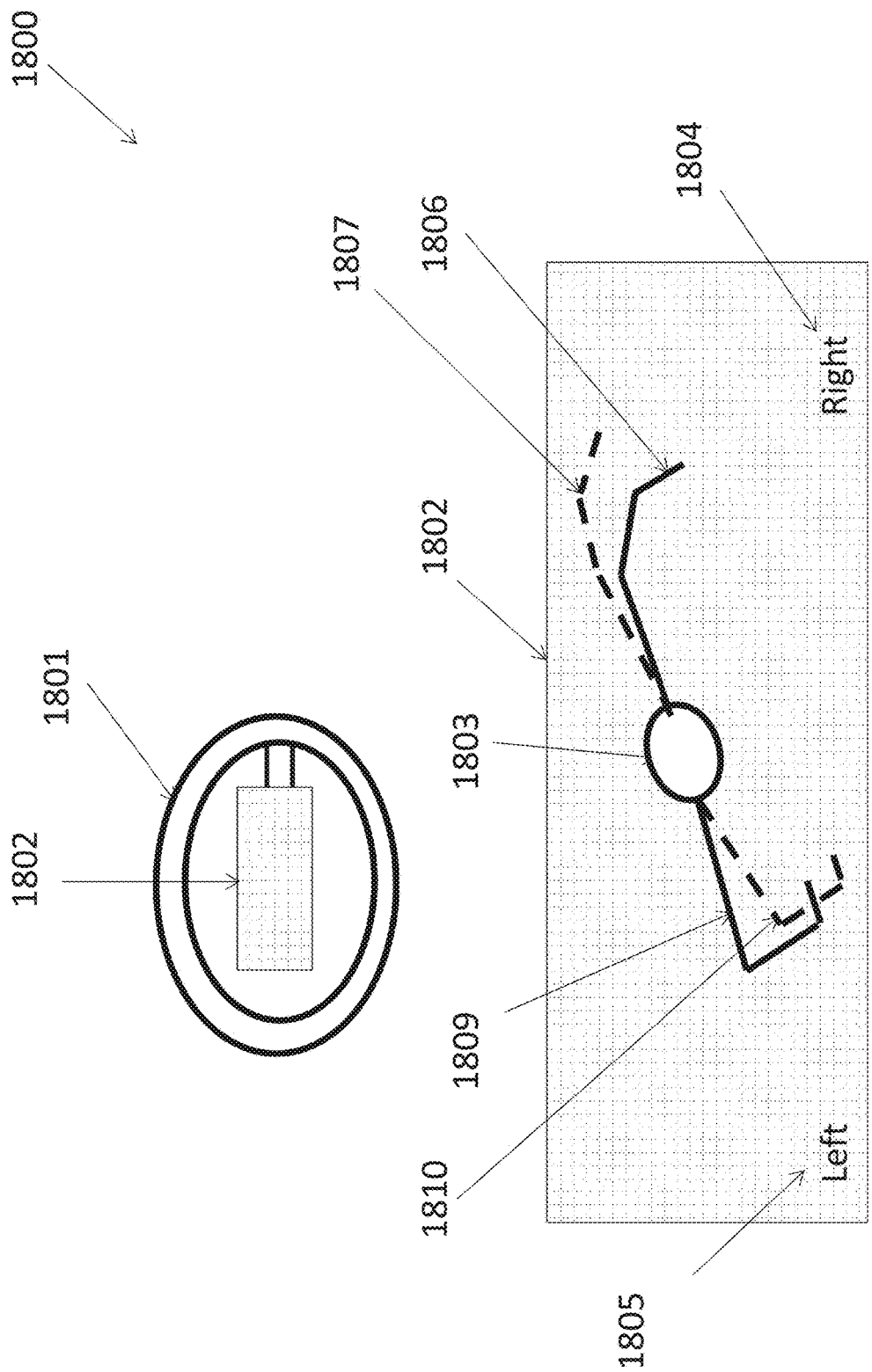
FIG. 18 is an illustration of the display of the 3-dimensional motions of the arms and hands of the swimmer measured by a multiplicity of microsensor modules placed on the swimmer's arms and hands while swimming.

More complicated 3-dimensional movements and forces of the swimmer during execution of the swimming strokes may or may not lend themselves to a simple graphic display and therefore the information provided to the swimmer will be provided in a more condensed manner. An embodiment 1800 is shown in FIG. 18. A partially transparent electronic display 1802 is made inside the eyepiece of the goggles 1801. The electronic display 1802 shown in expanded form at the bottom of the drawing of the embodiment 1800 provides an orientation as to the right 1804 and left 1805 sides of the swimmer 1803 who is represented by the oval in the center of the display since the swimmer 1803 is being projected along the length of the swimmer 1803. The correct technique of the swimmer's 1803 right 1806 and left 1809 arms and hands during the execution of the arm motions during the strokes are shown by continuous lines representing the right and 1806 and left 1809 arms and hands. These lines 1806 and 1809 are broken into three sections representing the upper arm, the lower arm and the hand, respectively. This is the arm and hand motions of a swimmer conducting excellent swimming technique. The actual swimmer's 1803 left arm and hand 1810 and right arm and hand 1807 are shown as dotted lines. It is noted that the correct swimming arm and hand motions differ from the actual arm and hand motions of the swimmer 1803. Therefore, this feedback allows the swimmer 1803 to understand how to improve their arm and hand motions so as to better emulate a correct arm motion during swimming. In the case of embodiment 1800, the swimmer can see that the right arm and hand motions are too high and wide in the air and the left arm and hand motions are too low in the water.

Similarly, pictorials of the arms and hand motions from the side of the swimmer can be provided using this type of display. Additionally, side and along the length of the swimmer pictorials of the legs and feet can be provided in a similar manner.

Figure 19:
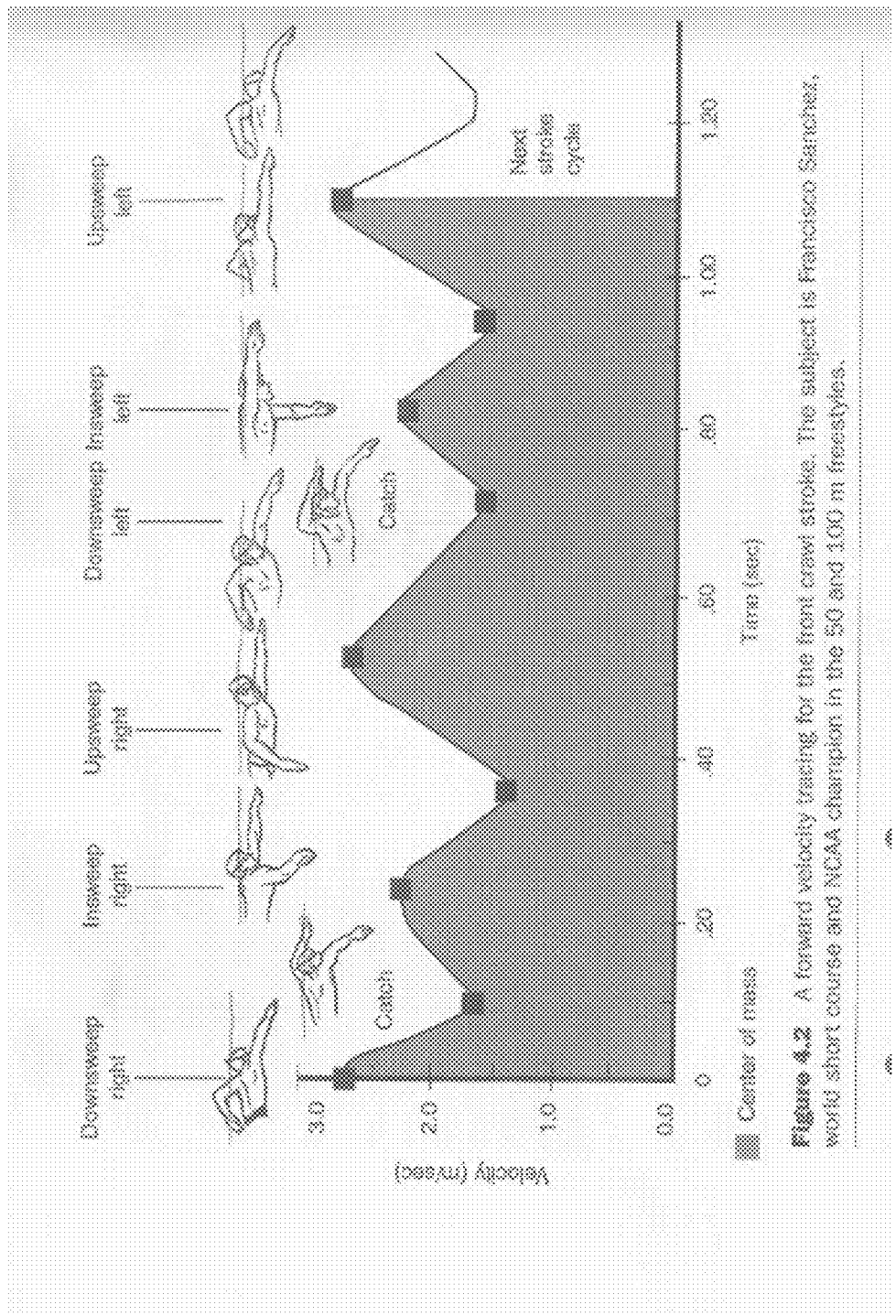
FIG. 19 is a representation of the swimmer's forward velocity when swimming the freestyle stoke showing the variation in the velocity of the swimmer during various portions of the stroke cycle.

Information about Swim Velocity During Stroke Cycles:

FIG. 19 is a plot of velocity as a function of time through a stoke cycle for freestyle swimming. The complete stoke cycle (both arms performing the stroke) occurs over a time period of about 1 sec. This is a typical number for a competitive swimmer for a complete stroke cycle. The peak velocity for this swimmer is a little below 3 m/s (during the upsweep) and falls to around 1.5 m/s during the catch phase of the stroke.

As can be seen from this diagram, the velocity of the swimmer varies considerably over the stroke cycle. Also, this swimmer has what is called a two-peak velocity profile. There is the first peak during insweep and a second and larger peak at the upsweep. This is fairly typical. Other swim strokes have similar variations in velocity versus time. Other swimmers have a single peak in their velocity profile. The number of peaks in a swimmer's velocity profile depends on their exact technique.

Obviously, going faster and being more efficient is desirable in swimming. However, knowing the velocity at each phase of the stroke cycle is extremely useful information since it allows a number of things to be diagnosed including: where the power in the cycle is generated; how much velocity is lost in recovery; how efficient is the swimmer; and more.

Therefore, a microsensor to measure velocity over the course of stroke cycles is useful. As seen in FIG. 19, the velocity of the swimmer ranges from about 1.5 to 3 m/s, with an average speed of around 2.2 m/s.

However, it is important to note that the velocity may be higher at the beginning of the race (perhaps due to the push off the starting blocks) as well as immediately after turns (when pushing off the walls during flip turns). Knowing the velocity of the swimmer over many cycles and at various points in an interval is also very useful since it provide information about how much velocity (and momentum) is gained (or lost) by the swimmer at the start, during turns and during the interval.

The peak average velocity of elite swimmers in sprints is about 3 to 3.2 m/s with a maximum overall velocity as high as 4 m/s. Therefore, the velocity sensor should probably have a dynamic range of at least 0 to 4 m/s. With regard to resolution, 0.1 m/s is sufficient. For sampling rates, the velocity has about 8 inflection points, over about 1 sec. Therefore, a sampling rate 16 times per second, or higher (i.e., 32 samples per see) is sufficient.

The velocity data can be presented to the swimmer in an electronic display in the goggles showing the part of the stroke cycle (e.g., insweep, downsweep, etc.) and the associated measured velocity during that part of the stroke cycle. This will allow the swimmer to know how their velocity at the important parts of the stroke cycle compares to elite swimmers. The microsesnor modules described above can provide the swimmer velocity data.

The microsensor modules can also be used for the starts and turns in swimming. The amount of explosive power that the swimmer uses to gain speed off of the starting blocks or walls at the start of the intervals can be determined using microsensor modules placed on the bottoms of the feet. The aerobatic maneuver performed by the swimmer jumping off the starting blocks can be measured using the microsensor modules on the swimmer's body. The loss of velocity as the swimmer enters the water can be measured as well as the streamlining of the swimmer after the water entry can all be measured using microsensor modules on the swimmer's body.

Turns in swimming can also be measured using the microsensor modules. The swimmer's velocity should not decrease as the swimmer approaches the wall for a turn (or the end of the interval for that matter) and this can be measured using the microsensor modules. As the swimmer performs a somersault during the turn and then uses an explosive force to push off of the wall can be measured using the microsensor modules. The streamlining of the swimmer including the undulating dolphins kicks used to propel the swimmer underwater for a few meters can be measured using the microsensor modules.

There are other types of microsensors that could be used to provide even more information to the swimmer so as to improve their technique. Included in these types of microsensors are the following: heart rate monitoring; temperature of the swimmer; VO2 maximum; hydration, lactose levels, and others.

Additionally, with respect to the correct technique used in swimming, it may be useful to capture data on elite swimmer's as a baseline reference that then can be used for comparing the actual athlete's performance to that of an elite athlete. This will allow the swimmer to know how their technique varies from that of the elite athletes.

It should be noted and understood that the present invention can be applied to any sport that requires good technique. Examples include: tennis, golf; hand ball; volley ball; baseball; racket ball; cricket; surfing; wind surfing; and others.

What is claimed:

1. A microsensor module comprising:
   a plurality of microsensors;
   a power supply;
   a communication circuit; and
   processing circuitry configured to:
      receive data measured by the plurality of microsensors;
      process the measured data to determine a plurality of different performance parameters related to technique of an athlete when swimming, wherein the plurality of different performance includes a horizontal body position of the athlete in the water and a body roll of the athlete as the athlete performs freestyle or backstroke swimming; and
      output, using the communication circuit, real-time information about the correctness of technique and performance level of the athlete performing the swimming determined based on comparing of the determined plurality of performance parameters to predetermined values,
   wherein two or more of the plurality of microsensors are encapsulated in a water-proof package that is attachable or adjoinable to the athlete's body.

2. The microsensor module of claim 1, wherein the plurality of microsensors include a plurality of different types of microsensors including one or more of: accelerometers; magnetometers; gyroscopes; force sensors; pressure sensors; velocity sensors; temperature sensors; and/or $VO_2$ maximum sensors.

3. The microsensor module of claim 1, wherein the plurality of microsensors includes two or more first microsensor configured to provide data for determining the horizontal body position of the athlete and two or more second microsensors configured to provide data for determining the body roll of the athlete.

4. The microsensor module of claim 1, wherein the plurality of microsensors are configured to be positioned on a portion of an athletes body that is horizontal to the surface of the water as the athlete performs freestyle or backstroke swimming.

5. The microsensor module of claim 1, wherein the one or more of the plurality of the microsensors are configured to measure three-dimensional motions of the athlete's arms and hands as the athlete performs the sport.

6. The microsensor module of claim 5, wherein the three-dimensional motions include velocity and acceleration.

7. The microsensor module of claim 1, wherein the one or more of the plurality of microsensors are configured to measure three-dimensional motions of the athlete's legs and.

8. The microsensor module of claim 7, wherein the three-dimensional motions include velocity and acceleration.

9. The microsensor module of claim 1, wherein the one or more of the plurality of microsensors are configured to measure the forces of the athlete's arms and hands as the athlete performs the sport.

10. The microsensor module of claim 1, wherein the one or more of the plurality of microsensors are configured to measure the forces of the athlete's legs and feet as the athlete performs the freestyle or backstroke swimming.

11. The microsensor module of claim 1, wherein the one or more of the plurality of microsensors are configured to measure a velocity of the athlete's body during each phase of motion as the athlete performs the sport.

12. A system including a plurality of microsensor modules of claim 1, the plurality of microsensors are attached to the athlete's body using an adhesive, a strap mechanism, or is woven into a fabric that the athlete can wear when performing the sport.

13. The system of claim 12, wherein two or more microsensor modules of the plurality of microsensor modules are wired together on the athlete's body so as to measure the athlete's performance and technique at various position on the athlete's body.

14. The microsensor module of claim 1, wherein the real time information is output to the athlete via a partially transparent electronic display attached onto glasses or goggles of the athlete electrically connected to an output of the microsensor module.

15. The microsensor module of claim 14, wherein the partially transparent electronic display is configured to provide graphical and alpha-numeric information to the athlete.

16. The microsensor module of claim 1, wherein the processing circuitry configured to: provide information about suggested technique based on the different performance parameters and technique and performance level of one or more sample athletes.

17. The microsensor module of claim 1, wherein the measured data of an athlete's technique and performance level is analyzed and directly compared to measured techniques of sample athletes in swimming.

18. The microsensor module of claim 1, wherein the microsensor module is configured to wirelessly communicate real-time information to a plurality of parties nearby by a radio frequency signal propagated from an antenna attached to the athlete's body and electrically connected to the microsensor module.

19. A method performed using a microsensor array comprising a plurality of microsensor modules including one or more microsensors, a power supply, a communication circuit, and processing circuitry encapsulated in a water-proof package that is configured to be attached or adjoined to an athlete's body, the method comprising:
    receiving data measured by the plurality of microsensors;
    processing the measured data to determine a plurality of different performance parameters related to technique of an athlete when swimming, wherein the plurality of different performance parameters includes a horizontal body position of the athlete in the water and a body roll of the athlete as the athlete performs freestyle or backstroke swimming; and
    output, using the communication circuit, real-time information about the correctness of technique and performance level of the athlete performing the swimming determined based on comparing of the determined plurality of performance para to predetermined values.

20. The method of claim 19, wherein the plurality of microsensors include a plurality of different types of microsensors including one or more of: accelerometers; magnetometers; gyroscopes; force sensors; pressure sensors; velocity sensors; temperature sensors; and/or $VO_2$ maximum sensors.

21. The method of claim 19, wherein the real-time information about the correctness of technique and performance level is provided to the athlete using a partially transparent electronic display attached onto glasses or goggles of the athlete electrically connected to an output of the microsensor module that provides graphical and alpha-numeric information to the athlete when performing the swimming.

22. The method of claim 19, wherein three-dimensional motions of various parts of the athlete's body and the athlete's entire body are measured, analyzed and provided to the athlete while the athlete performs the swimming.

23. The method of claim 19, wherein the plurality of microsensors includes two or more first microsensor configured to provide data for determining the horizontal body position of the athlete and two or more second microsensors configured to provide data for determining the body roll of the athlete.

24. A system comprising a plurality of microsensor modules, wherein each microsensor module comprises:
    a plurality of microsensors configured to collect data;
    signal processing circuits;
    a power supply; and
    communication circuits;
    wherein each microsensor module is encapsulated in a water-proof package that is configured to be attached or adjoined to an athlete's body and determine various performance parameters related to athlete's technique when performing swimming based on measurements received from the plurality of microsensors, the plurality of different performance parameters including a horizontal body position of the athlete in the water and a body roll of the athlete as the athlete performs freestyle or backstroke swimming,
    wherein the communication circuits is configured to provide real-time information about the correctness of technique and performance level of an athlete performing the swimming determined based on comparing of the determined plurality of performance parameters to predetermined values.

25. The system of claim 24, wherein the performance parameters are determined based on measured data on athletic technique and performance from sample athletes while performing swimming.

26. The system of claim 24, wherein the plurality of microsensors include one or more of: accelerometers; magnetometers; gyroscopes; force sensors; pressure sensors; velocity sensors; temperature sensors; and $VO_2$ maximum sensors.

27. The system of claim 24, wherein the real-time information about the athlete's technique and performance level is provided to the athlete using a partially transparent electronic display attached onto glasses or goggles of the athlete that is electrically connected to outputs of the microsensor modules that is configured to provide graphical and alpha-numeric information to the athlete when performing the swimming.

28. The system of claim 24, wherein three-dimensional motions of various parts of the athlete's body and the athlete's entire body are measured, analyzed and provided to the athlete while the athlete performs the swimming.

29. The system of claim 24, wherein the plurality of microsensors includes two or more first microsensor configured to provide data for determining the horizontal body position of the athlete and two or more second microsensors configured to provide data for determining the body roll of the athlete.

30. The system of claim 24, wherein the microsensor module is configured to provide information about suggested technique based on the different performance parameters and technique and performance level of one or more sample athletes.

31. The system of claim 24, wherein the measured performance parameters related to the athlete's technique is analyzed and directly compared to measured techniques of sample athletes in the swimming.

* * * * *